(12) United States Patent
Shao et al.

(10) Patent No.: US 12,153,037 B2
(45) Date of Patent: Nov. 26, 2024

(54) METHOD AND SYSTEM FOR MEASURING ENERGY OF NATURAL GAS BASED ON REDUCED DATA DEVIATION

(71) Applicant: CHENGDU QINCHUAN IOT TECHNOLOGY CO., LTD., Sichuan (CN)

(72) Inventors: Zehua Shao, Chengdu (CN); Haitang Xiang, Chengdu (CN); Xiaojun Wei, Chengdu (CN); Yaqiang Quan, Chengdu (CN)

(73) Assignee: CHENGDU QINCHUAN IOT TECHNOLOGY CO., LTD., Chengdu (CN)

( * ) Notice: Subject to any disclaimer, the term of this patent is extended or adjusted under 35 U.S.C. 154(b) by 0 days.

(21) Appl. No.: 18/363,724

(22) Filed: Aug. 1, 2023

(65) Prior Publication Data
US 2023/0408481 A1    Dec. 21, 2023

Related U.S. Application Data

(63) Continuation of application No. 17/649,335, filed on Jan. 28, 2022, now Pat. No. 11,796,528.

(30) Foreign Application Priority Data

Feb. 4, 2021   (CN) .......................... 202110154143.8
Jan. 14, 2022  (CN) .......................... 202210045114.2

(51) Int. Cl.
*G01N 33/22*     (2006.01)
*G06F 30/27*     (2020.01)

(52) U.S. Cl.
CPC ........... *G01N 33/225* (2013.01); *G06F 30/27* (2020.01)

(58) Field of Classification Search
CPC .............................. G01N 33/225; G06F 30/27
See application file for complete search history.

(56) References Cited

U.S. PATENT DOCUMENTS

| 4,821,557 A | 4/1989 | Beeson, III |
| 6,612,186 B1 | 9/2003 | Patten et al. |

(Continued)

FOREIGN PATENT DOCUMENTS

| AU | 5433899 A | 3/2000 |
| CN | 1401071 A | 3/2003 |

(Continued)

OTHER PUBLICATIONS

Kim, S.J.; Jang, S.P. Experimental and numerical analysis of heat transfer phenomena in a sensor tube of a mass flow controller. Int. J. Heat Mass Transf. 2001, 44, 1711-1724; (Year: 2001).*

(Continued)

*Primary Examiner* — Michael J Dalbo
*Assistant Examiner* — Kaleria Knox
(74) *Attorney, Agent, or Firm* — METIS IP LLC

(57) ABSTRACT

The disclosure provides a method for measuring energy of natural gas, including determining first energy per unit volume of the target natural gas based on the carbon content; obtaining combustible component information in the target natural gas, and determining second energy per unit volume of the target natural gas based on the combustible component information; determining a difference between the first energy per unit volume and the second energy per unit volume; based on the difference, determining whether the first energy per unit volume and the second energy per unit volume are accurate by a deviation determination model; and if the first energy per unit volume and the second energy per unit volume are accurate, determining the energy of the target natural gas based on the first energy per unit volume, (Continued)

the second energy per unit volume, and the volume of the target natural gas.

18 Claims, 6 Drawing Sheets

(56) References Cited

U.S. PATENT DOCUMENTS

| | | | |
|---|---|---|---|
| 9,581,479 B2* | 2/2017 | Hanks | G01F 1/68 |
| 2009/0028209 A1 | 1/2009 | Feitisch et al. | |
| 2009/0249860 A1 | 10/2009 | Tanikawa | |
| 2014/0109686 A1 | 4/2014 | Ramsay | |
| 2014/0303909 A1 | 10/2014 | Hanks et al. | |
| 2020/0302558 A1 | 9/2020 | Shao | |

FOREIGN PATENT DOCUMENTS

| | | | |
|---|---|---|---|
| CN | 103557911 A | * | 2/2014 |
| CN | 105973337 A | | 9/2016 |
| CN | 106706064 A | | 5/2017 |
| CN | 106706084 A | | 5/2017 |
| CN | 108534871 A | | 9/2018 |
| CN | 208333625 U | | 1/2019 |
| CN | 111766327 A | | 10/2020 |
| CN | 111853543 A | | 10/2020 |
| CN | 112381534 A | | 2/2021 |
| CN | 112836178 A | | 5/2021 |
| CN | 112946167 A | | 6/2021 |
| DE | 102004020287 A1 | | 11/2005 |
| EP | 1391703 A1 | | 2/2004 |
| WO | 0011465 A1 | | 3/2000 |
| WO | 2004046660 A2 | | 6/2004 |
| WO | 2013017876 A1 | | 2/2013 |

OTHER PUBLICATIONS

Ficco, G.; Celenza, L.; Dell'Isola, M.; Frattolillo, A.; Vigo, P. Experimental evaluation of thermal mass smart meters influence factors. J. Nat. Gas Sci. Eng. 2016, 32, 556-565. (Year: 2016).*

Rupik, K.; Kutin, J.; Bajsi'c, I. A Method for Gas Identification in Thermal Dispersion Mass Flow Meters. Strojniski Vestnik J. Mech. Eng. 2014, 60, 607-616. (Year: 2014).*

"Energy Measurement Using Ultrasonic Flow Measurement & Chromatography" disclose the Table 1 components gas, Temperature & Pressure. (Year: 2019).*

Jaworski "Study of the Effects of Changes in Gas Composition as Well as Ambient and Gas Temperature on Errors of Indications of Thermal Gas Meters". Jul. 31, 2020, pp. 2-23. (Year: 2020).*

Taras Koturbash et al., Development of New Instant Technology of Natural Gas Quality Determination, Proceedings of the ASME 2013 Power Conference, 2013, 6 pages.

Shen, Chao, Evaluation of Uncertainty in Natural Gas Energy Measurement, Metrology & Measurement Technique, 48(1): 115-118, 2021.

Shao, Zehua et al., Electricity Self-supply Device of IoT Intelligent Gas Meter, Gas Equipment and Materials, 2021, 4 pages.

Jim Beeson et al., Natural Gas Energy Measurements with Flow Calculators and Chromatographic Analyzers, Foreign Oilfield Engineering, 1996, 5 pages.

Si, Qiang, Discussion on the Application of Natural Gas Measurement Error and Energy Measurement Method, Chemical Management, 2020, 3 pages.

Yang, Xuhui, Natural Gas Capacity Metering System, Proceedings of the 7th Academic Conference on Industrial Instrumentation and Automation, 2006, 3 pages.

Li, KE et al., Research on Application of Natural Gas Energy Measurement and Assignment Calculation, Metrology Technology, 2010, 4 pages.

G. Ficco et al., Uncertainty Analysis of Energy Measurements in Natural Gas Transmission Networks, Flow Measurement and Instrumentation, 42: 58-68, 2015.

Sung Jin Kim et al., Experimental and Numerical Analysis of Heat Transfer Phenomena in a Sensor Tube of a Mass Flow Controller, International Journal of Heat and Mass Transfer, 44: 1711-1724, 2001.

G. Ficco et al., Experimental Evaluation of Themal Mass Smart meters Infuence Factors, Journal of Natural Gas Science and Engineering, 32: 556-565, 2016.

Klemen Rupnik et al., A Method for Gas Identfication in Thermal Dispersion Mass Flow Meters, Strojniki vestnik-Journal of Mechanical Engineering, 60(9): 607-616, 2014.

Jacek Jaworski et al., Study of the Effects of Changes in Gas Composition as Well as Ambient and Gas Temperatureon on Errors of Indications of Thermal Gas Meters, Energies, 2020, 23 pages.

"Energy Measurement Using Ultrasonic Flow Measurement &Chromatography", OIL & GAS, 2019, 4 pages.

M. Viswanathan et al., Development, Modeling and Certain Investigations on Thermal Mass Flow Metres, Flow Measurement and Instrumentation, 12: 353-360, 2002.

First Office Action in Chinese Application No. 202110154143.8 mailed on Jan. 17, 2022, 16 pages.

Yu, Danfeng et al., Transformation and Upgrading of Natural-gas Energy Metering for Yacheng 13-1 Gasfield, Natural gas Technology Economy, 5(6): 50-52&79, 2011.

* cited by examiner

METHOD AND SYSTEM FOR MEASURING ENERGY OF NATURAL GAS BASED ON REDUCED DATA DEVIATION

CROSS-REFERENCE RELATED APPLICATION

This application is a Continuation of U.S. patent application Ser. No. 17/649,335, filed on Jan. 28, 2022, which claims the priority of the Chinese Patent Application No. 202110154143.8 filed on Feb. 4, 2021 and the Chinese Patent Application No. 202210045114.2 filed on Jan. 14, 2022, the contents of which are entirely incorporated herein by reference.

TECHNICAL FIELD

The present disclosure relates to the field of energy measuring, and more particularly to methods and systems for measuring energy of natural gas.

BACKGROUND

Natural gas resources are highly efficient and clean, and have been widely used in industrial fuels, process production, and urban household gas. However, natural gas resources are limited, and how to accurately measure the natural gas energy used is very important for rational utilization of natural gas resources and reduction of natural gas energy waste.

Therefore, it is desirable to provide an accurate method and system for measuring energy of natural gas.

SUMMARY

The present disclosure provides a method for measuring energy of natural gas, and the method includes obtaining the carbon content and volume of the target natural gas provided for use; determining the first energy per unit volume of the target natural gas based on the carbon content; determining first energy per unit volume of the target natural gas based on the carbon content; obtaining information on combustible components in the target natural gas, and determining second energy per unit volume of the target natural gas based on the information on combustible components; determining a difference between the first energy per unit volume and the second energy per unit volume; based on the difference between the first energy per unit volume and the second energy per unit volume, determining whether the first energy per unit volume and the second energy per unit volume are accurate by a deviation determination model; and in response to determining that the first energy per unit volume and the second energy per unit volume are accurate, determining energy of the target natural gas based on the first energy per unit volume, the second energy per unit volume, and the volume of the target natural gas.

In some embodiments, the determining the first energy per unit volume of the target natural gas based on the carbon content comprises: obtaining an ambient temperature and an air oxygen content when the target natural gas is provided for use, and a transmission rate of the target natural gas when provided; and determining the first energy per unit volume by a first prediction model based on the ambient temperature, the air oxygen content, the transmission rate, and the carbon content.

In some embodiments, wherein the first prediction model is obtained by a training process, the training process comprising: obtaining at least one training sample, wherein each of the at least one training sample includes a sample carbon content of a sample natural gas, a sample ambient temperature and a sample air oxygen content when the sample natural gas was provided in use, a sample transmission rate when the sample natural gas is provided and a sample energy per unit volume value of the sample natural gas, wherein the sample energy per unit volume value is determined by the actual combustion of the sample natural gas; and obtaining the first prediction model based on the at least one training sample.

In some embodiment, wherein the determining the second energy per unit volume of the target natural gas based on the combustible composition information comprises: obtaining the ambient temperature and air oxygen content when the target natural gas is provided for use, and the transmission rate of the target natural gas when provided; and determining the second energy per unit volume by a second prediction model based on the ambient temperature, the air oxygen content, the transmission rate, and the combustible composition information.

In some embodiment, wherein the training process of the second prediction model comprises: obtaining at least one training sample, wherein each of the at least one training sample includes a sample combustible composition information of sample natural gas, the sample ambient temperature and the sample air oxygen content when the sample natural gas was provided in use, the sample transmission rate when the sample natural gas is provided and the sample energy per unit volume value of the sample natural gas, wherein the sample energy per unit volume value is determined by the actual combustion of the sample natural gas; and obtaining the second prediction model based on the at least one training sample.

In some embodiment, wherein, based on the difference between the first energy per unit volume and the second energy per unit volume, determining whether the first energy per unit volume and the second energy per unit volume are accurate through a deviation determination model comprises: obtaining the ambient temperature and air oxygen content when the target natural gas is provided for use, and the transmission rate of the target natural gas when provided; and determining whether the first energy per unit volume and the second energy per unit volume are accurate by the deviation determination model, based on the ambient temperature, the air oxygen content, the transmission rate, and the difference between the first energy per unit volume and the second energy per unit volume.

In some embodiment, wherein the training process of the deviation determination model comprises: obtaining at least one training sample, wherein each of the at least one training sample includes a difference between the sample first energy per unit volume and the sample second energy per unit volume of the sample natural gas, the sample ambient temperature and the sample air oxygen content when the sample natural gas is provided for use, the sample transmission rate when the sample natural gas is provided and the sample energy per unit volume value of the sample natural gas, wherein the sample energy per unit volume value is determined by the actual combustion of the sample natural gas; and obtaining the deviation determination model based on the at least one training sample.

In some embodiments, wherein based on the difference between the first energy per unit volume and the second energy per unit volume, determining whether the first energy per unit volume and the second energy per unit volume are accurate by a deviation determination model includes determining a deviation coefficient by a deviation determination model based on the difference between the first energy per unit volume and the second energy per unit volume; and the method further comprises: in response to determining that the first energy per unit volume and the second energy per unit volume are inaccurate, obtaining corrected energy per unit volume by a correction model based on the first energy per unit volume, the second energy per unit volume and the deviation coefficient.

In some embodiment, wherein the training process of the correction model comprises: obtaining at least one training sample, wherein each of the at least one training sample includes the sample first energy per unit volume of the sample natural gas, the sample second energy per unit volume, the sample deviation coefficient corresponding to the sample natural gas and the sample energy per unit volume of the sample natural gas, wherein the sample energy per unit volume value is determined by the actual combustion of the sample natural gas; and obtaining the correction model based on the at least one training sample.

The present disclosure provides a system for measuring energy of natural gas, the system comprising: at least one storage device, including a set of instructions; at least one processor in communication with the at least one storage device, wherein when the at least one storage device is executed, the at least one processor is configured to cause the system to perform at least one operation comprising: obtaining a carbon content and volume of target natural gas provided for use; determining first energy per unit volume of the target natural gas based on the carbon content; obtaining information on combustible components in the target natural gas, and determining second energy per unit volume of the target natural gas based on the information on combustible components; determining a difference between the first energy per unit volume and the second energy per unit volume; based on the difference between the first energy per unit volume and the second energy per unit volume, determining whether the first energy per unit volume and the second energy per unit volume are accurate by a deviation determination model; and in response to determining that the first energy per unit volume and the second energy per unit volume are accurate, determining energy of the target natural gas based on the first energy per unit volume, the second energy per unit volume, and the volume of the target natural gas.

In some embodiment, wherein the determining, based on the carbon content, the first energy per unit volume of the target natural gas comprises: obtaining an ambient temperature and an air oxygen content when the target natural gas is provided for use, and a transmission rate of the target natural gas when provided; and determining the first energy per unit volume by a first prediction model based on the ambient temperature, the air oxygen content, the transmission rate, and the carbon content.

In some embodiment, wherein the first prediction model is obtained by a training process, the training process comprising: obtaining at least one training sample, wherein each of the at least one training sample includes a sample carbon content of a sample natural gas, a sample ambient temperature and a sample air oxygen content when the sample natural gas was provided in use, a sample transmission rate when the sample natural gas is provided and a sample energy per unit volume value of the sample natural gas, wherein the sample energy per unit volume value is determined by the actual combustion of the sample natural gas; and obtaining the first prediction model based on the at least one training sample.

In some embodiment, the determining the second energy per unit volume of the target natural gas based on the combustible composition information comprises: obtaining the ambient temperature and air oxygen content when the target natural gas is provided for use, and the transmission rate of the target natural gas when provided; and determining the second energy per unit volume by a second prediction model based on the ambient temperature, the air oxygen content, the transmission rate, and the combustible composition information.

In some embodiment, the training process of the second prediction model comprises: obtaining at least one training sample, wherein each of the at least one training sample includes a sample combustible composition information of sample natural gas, the sample ambient temperature and the sample air oxygen content when the sample natural gas was provided in use, the sample transmission rate when the sample natural gas is provided and the sample energy per unit volume value of the sample natural gas, wherein the sample energy per unit volume value is determined by the actual combustion of the sample natural gas; and obtaining the second prediction model based on the at least one training sample.

In some embodiment, based on the difference between the first energy per unit volume and the second energy per unit volume, determining whether the first energy per unit volume and the second energy per unit volume are accurate through a deviation determination model comprises: obtaining the ambient temperature and air oxygen content when the target natural gas is provided for use, and the transmission rate of the target natural gas when provided; and determining whether the first energy per unit volume and the second energy per unit volume are accurate by the deviation determination model, based on the ambient temperature, the air oxygen content, the transmission rate, and the difference between the first energy per unit volume and the second energy per unit volume.

In some embodiment, the training process of the deviation determination model comprises: obtaining at least one training sample, wherein each of the at least one training sample includes a difference between the sample first energy per unit volume and the sample second energy per unit volume of the sample natural gas, the sample ambient temperature and the sample air oxygen content when the sample natural gas is provided for use, the sample transmission rate when the sample natural gas is provided and the sample energy per unit volume value of the sample natural gas, wherein the sample energy per unit volume value is determined by the actual combustion of the sample natural gas; and obtaining the deviation determination model based on the at least one training sample.

In some embodiments, a deviation coefficient is determined by a deviation determination model based on the difference between the first energy per unit volume and the second energy per unit volume; and the method further comprises: in response to determining the first energy per unit volume and the second energy per unit volume are inaccurate, based on the first energy per unit volume, the second energy per unit volume and the deviation coefficient, the corrected energy per unit volume is obtained through a correction model.

In some embodiments, the obtaining process of the correction model includes: acquiring at least one training sample, wherein each of the at least one training sample includes a sample first energy per unit volume, a sample second energy per unit volume of the sample natural gas, a sample deviation coefficient corresponding to the sample natural gas, and a sample energy per unit volume of the sample natural gas, the sample energy per unit volume value being determined by the actual combustion of the sample natural gas; and based on the at least one training sample, obtaining the correction model.

The present disclosure provides a non-transitory computer-readable storage medium, the non-transitory computer-readable storage medium including at least one set of instructions, wherein the at least one set of instructions is stored by one or more of a computing device. When executed by the above processor, the at least one set of instructions causes the computing device to execute a method, the method comprising: obtaining carbon content and volume of target natural gas provided in use; determining first energy per unit volume of the target natural gas based on the carbon content; obtaining information on combustible components in the target natural gas, and determining second energy per unit volume of the target natural gas based on the information on combustible components; determining a difference between the first energy per unit volume and the second energy per unit volume; based on the difference between the first energy per unit volume and the second energy per unit volume, determining whether the first energy per unit volume and the second energy per unit volume are accurate by a deviation determination model; and in response to determining that the first energy per unit volume and the second energy per unit volume are accurate, determining energy of the target natural gas based on the first energy per unit volume, the second energy per unit volume, and the volume of the target natural gas.

Some additional features of the present disclosure may be explained in the following description. Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components. But do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Figure 2:
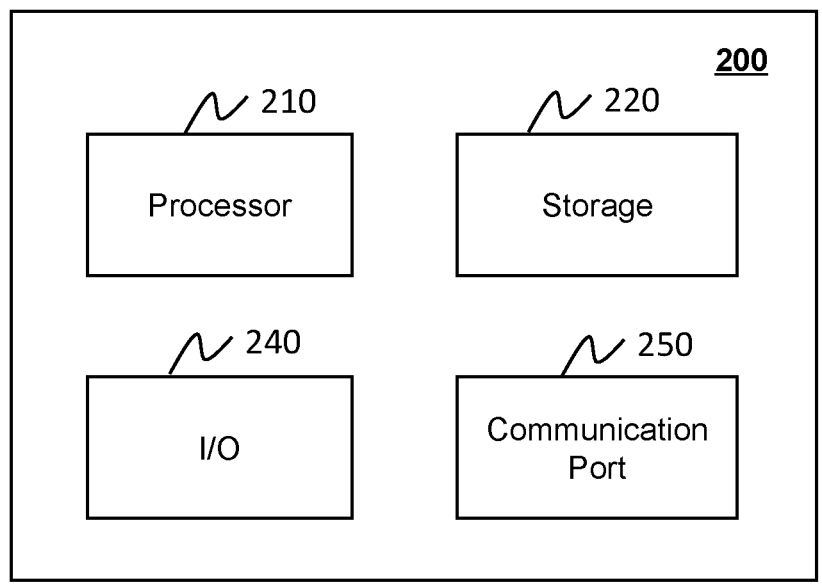
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. When a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
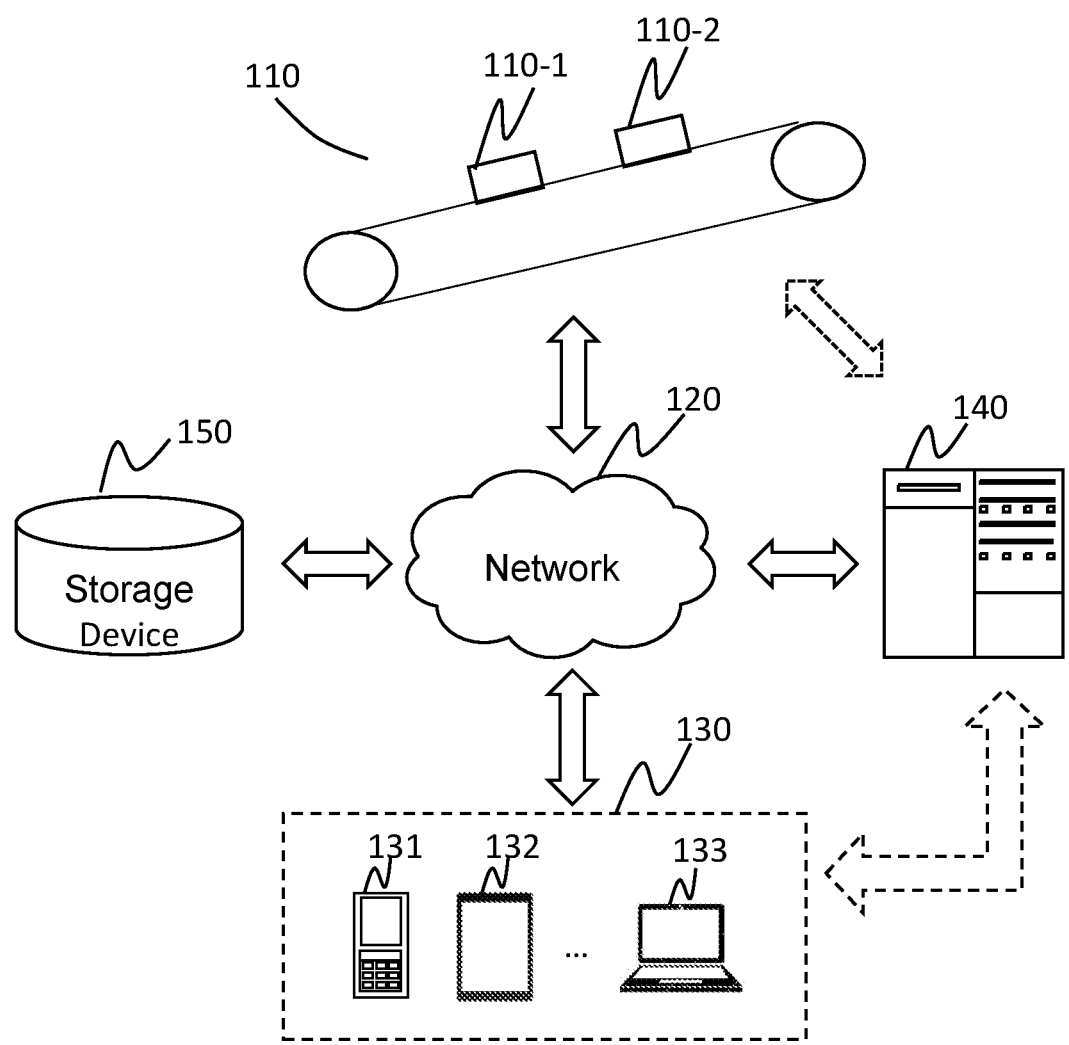
FIG. 1 is a schematic diagram illustrating an application scenario of an exemplary system for measuring energy of natural gas according to some embodiments of the present disclosure.

FIG. 1 is a schematic diagram illustrating an application scenario of an exemplary system for measuring energy of natural gas according to some embodiments of the present disclosure. As shown in FIG. 1, an application scenario 100 of a system for measuring energy of natural gas (also referred to as the natural gas energy metering system) may include a metering device of natural gas 110, a network 120, a terminal 130, a processing device 140 and a storage device 150. The connection between the components in the application scenario 100 of the natural gas energy metering system may be variable. As shown in FIG. 1, the metering device of natural gas 110 may be coupled to the processing device 140 via the network 120. For example, the metering device of natural gas 110 may be directly connected to the processing device 140. As another example, the storage device 150 may be connected to the processing device 140 directly or through the network 120. As still another example, the terminal 130 may be directly connected to the processing device 140 (as shown by the dashed arrow of the connection terminal 130 and the processing device 140), or may be connected to the processing device 140 via the network 120.

The metering device of natural gas 110 may be configured to collect data related to natural gas. In some embodiments, the metering device of natural gas 110 may include a detecting device of carbon content 110-1 (e.g., chromatographic detector) and a volume detecting device 110-2 (e.g., ultrasonic volume measuring instrument). The detecting device of carbon content 110-1 may be configured to obtain a carbon content of natural gas. The volume detecting device 110-2 may be configured to obtain the volume of natural gas. In some embodiments, the metering device of natural gas 110 may also include a temperature monitoring apparatus provided on a natural gas pipeline or a natural gas pipeline, an oxygen concentration monitoring device, a natural gas transmission speed monitor (FIG. 1 is not shown), or the like. The temperature monitoring device may be configured to obtain ambient temperature when natural gas is provided for use. The oxygen concentration monitoring device may be configured to obtain the oxygen content of the air when the natural gas is provided for use. The monitoring device of natural gas transmission rate may be configured to obtain the transmission rate at which natural gas is being provided.

The network 120 may include any suitable network that can facilitate the information and/or data exchange of the application scenario 100 of the system for measuring energy of natural gas. In some embodiments, one or more components of application scenario 100 of the system for measuring energy of natural gas (e.g., the metering device of natural gas 110, the terminal 130, the processing device 140, the storage device 150) may exchange information and/or data with each other over the network 120. For example, the processing device 140 may obtain data related to natural gas from the metering device of natural gas 110 via the network 120. For example, the processing device 140 may obtain user instructions from the terminal 130 via the network 120.

The terminal 130 may include a mobile device 131, a tablet computer 132, a laptop computer 133, or the like, or any combination thereof. In some embodiments, the terminal 130 may be part of the processing device 140.

The processing device 140 may process data and/or information obtained from the metering device of natural gas 110, the terminal 130, and/or the storage device 150. For example, the processing device 140 may acquire carbon content and volume of the target natural gas supplied to use. The processing device 140 may determine the first energy per unit volume based on the carbon content of the target natural gas. The processing device 140 may also obtain the combustible component information in the target natural gas, and determine the second energy per unit volume of the target natural gas based on the combustible component information. The processing device 140 may also determine whether the first energy per unit volume and the second energy per unit volume are accurate by the deviation determination model based on the difference between the first energy per unit volume and the second energy per unit volume. In response to determining that the first energy per unit volume and the second energy per unit volume are accurate, the processing device 140 may determine the target natural gas energy based on the volume of the target natural gas, the first energy per unit volume, and the second energy per unit volume of the target natural gas. In some embodiments, the processing device 140 may be a single server or server group. The server group can be centralized or distributed. In some embodiments, the processing device 140 may be local or remote.

The storage device 150 can store data, instructions, and/or any other information. In some embodiments, the storage device 150 may store data obtained from the terminal 130 and/or the processing device 140. In some embodiments, the storage device 150 may store the processing device 140 to perform or implement data and/or instructions for performing the exemplary methods described in the present disclosure.

In some embodiments, the storage device 150 may be connected to network 120 to communicate with one or more other components (e.g., the processing device 140, the terminal 130) in the application scenario 100 of the system for measuring energy of natural gas. One or more components of the application scenario 100 of the system for measuring energy of natural gas can access the data or instructions stored in the storage device 150 via the network 120. In some embodiments, the storage device 150 may be directly connected to one or more other components in the application scenario 100 of the system for measuring energy of natural gas or communication (e.g., the processing device 140, the terminal 130). In some embodiments, the storage device 150 may be part of the processing device 140.

In some embodiments, the metering device of natural gas 110 may include the processing device 140. In some embodiments, the metering device of natural gas 110 may include the storage device 150.

The description of the application scenario 100 on the natural gas energy metering system is intended to be illustrative, not the scope of the present disclosure. Many alternatives, modifications, and changes will be apparent to those of ordinary skill in the art. The features, structures, methods, and other features of the exemplary embodiments described herein can be combined in a variety of ways to obtain additional and/or alternative exemplary embodiments. For example, the processing device 140 and metering device of natural gas 110 may be integrated into a single device. However, these changes and modifications do not deviate from the scope of the present disclosure.

FIG. 2 is a schematic diagram illustrating exemplary hardware and/or software components of an exemplary computing device according to some embodiments of the present disclosure, wherein the processing device 140 may be implemented on the computing device. As shown in FIG. 2, computing device 200 may include a processor 210, a memory 220, an input/output (I/O) 230, and a communication port 240.

The processor 210 may perform computer instructions (e.g., program code) and perform function of the processing device 140 in accordance with the techniques described herein. The computer instruction can include, for example, routine, programs, objects, components, data structures, processes, modules, and functions that perform specific functions described herein. For example, the processor 210 may process data obtained from any other component of the metering device of natural gas 110, the terminal 130, the storage device 150, and/or the application scenario 100 of the system for measuring energy of natural gas. In some embodiments, the processor 210 may include one or more hardware processors, such as microcontrollers, microprocessors, reduced instruction set computers (RISCs), application-specific integrated circuits (ASICs), application-specific instruction-set processors (ASIPs)), central processing unit (CPU), image processing unit (GPU), physical operation processing unit (PPU), microcontroller unit, digital signal processor (DSP), field-programmable gate array (FPGA), advanced RISC machine (ARM), programmable logic device (PLD), and any circuits and processors capable of performing one or more functions, or the like, or any combination thereof.

Just for explanation, only one processor is described in the computing device 200. However, it should be noted that the computing device 200 in the present disclosure may also include a plurality of processors. Thus, operations and/or method steps performed by one processor as described in this application may also be performed by multiple processors collectively or separately. For example, if in the present disclosure, the processor of the computing device 200 performs steps A and B, it should be understood that steps A and B may also be performed jointly or independently by two or more different processors of the computing device 200 (e.g., step A is performed by a first processor, step B is performed by a second processor, or steps A and B are performed jointly by the first and second processors).

The memory 220 may store data or information obtained from any other component of the metering device of natural gas 110, the terminal 130, the storage device 150, and/or the application scenario 100 of the system for measuring energy of natural gas. In some embodiments, the memory 220 may include a large-capacity storage device, a removable storage device, a volatile read/write memory, a read-only memory (ROM), or the like, or any combination thereof.

The I/O 230 may input and/or output signals, data, information, or the like. In some embodiments, the I/O 230 may implement interaction with the user and the processing device 140. In some embodiments, the I/O 230 may include an input device and an output device. Exemplary input devices may include a keyboard, a mouse, a touch screen, a microphone, or the like, or any combination thereof. Exemplary output devices may include display devices, speakers, printers, projectors, or the like, or any combination thereof. Examples of display devices may include liquid crystal displays (LCDs), light-emitting diode (LED) based displays, flat panel displays, curved screens, television devices, cathode ray tubes (CRTs), touch screen screens, or the like, or combinations thereof.

The communication port 240 may be connected to a network (e.g., network 120) to facilitate data communication. The communication port 240 may establish a connection between the processing device 140 and the metering device of natural gas 110, the terminal 130, and/or the storage device 150. The connection may be a wired connection, a wireless connection, any other communication connection that enables data transmission and/or reception, and/or a combination of these connections.

Figure 3:
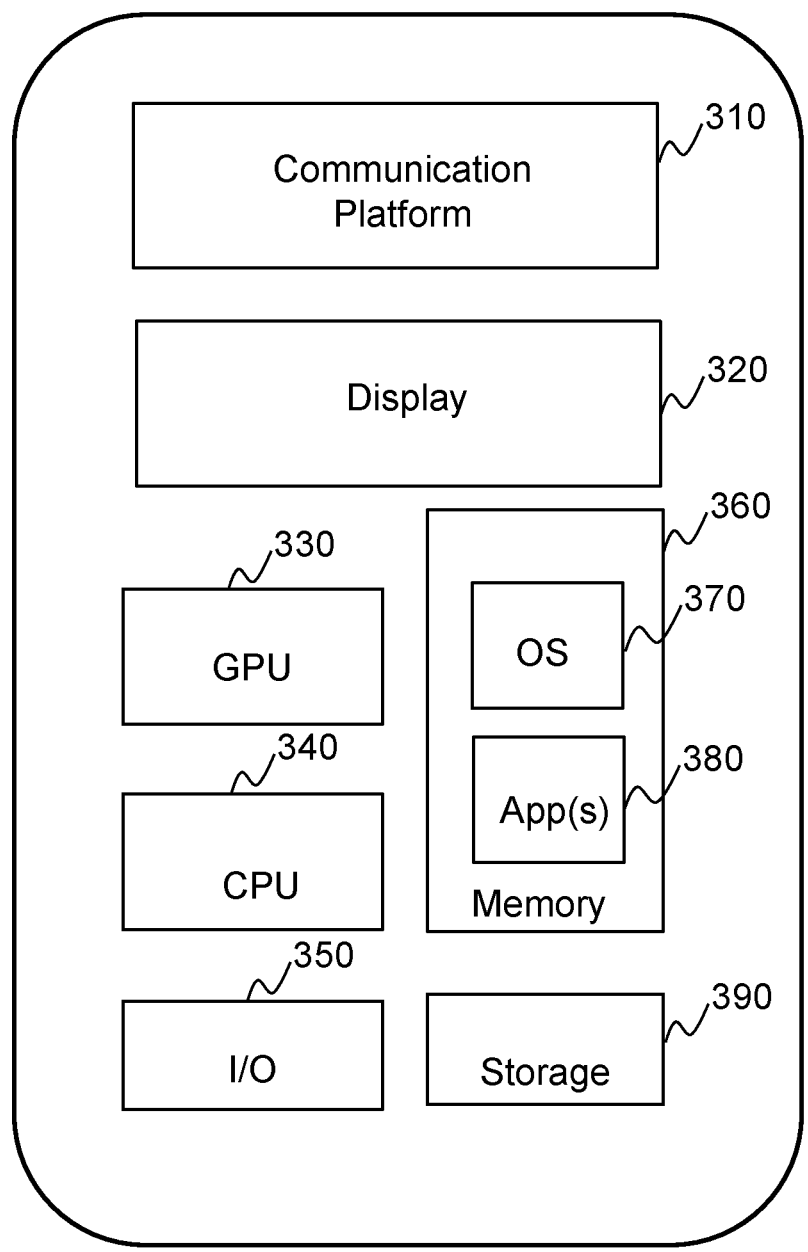
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the terminal 130 may be implemented on the mobile device.

As shown in FIG. 3, mobile device 300 may include a communication platform 310, a display 320, a graphics processing unit (GPU) 330, a central processing unit (CPU) 340, an I/O 350, a memory 360, and a storage 390. In some embodiments, any other suitable components, including but not limited to a system bus or controller (not shown), may also be included in the mobile device 300. In some embodiments, mobile operating system 370 (e.g., iOS, Android, Windows Phone, etc.) and one or more application 380 may be downloaded from the memory 390 to the memory 360 and executed by the CPU 340. The application 380 may include a browser or any other suitable mobile application for receiving and browsing information or other information related to data processing from the processing device 140. User interaction with the information flow may be accomplished via the I/O 350 and provided via the network 120 to the processing device 140 and/or other components of the application scenario 100 of the system for measuring energy of natural gas.

In order to implement the various modules, units, and functions described in the present disclosure, the computer hardware platform may be used as a hardware platform for one or more components described in the present disclosure. Computers with user interface elements may be used to implement personal computer (PC) or any other type of workstation or terminal device. If the computer is properly programmed, the computer may also be used as a server.

Figure 4:
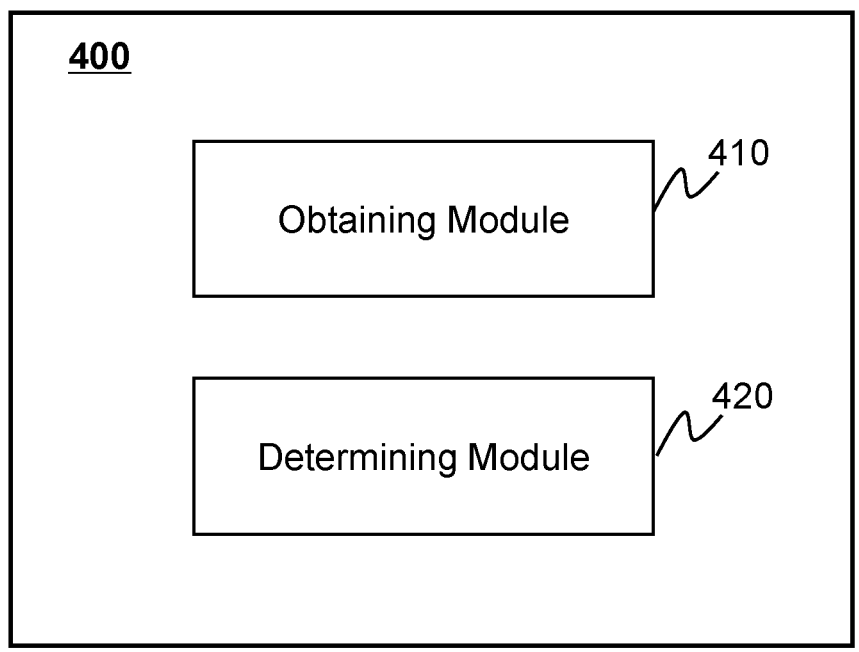
FIG. 4 is a block diagram illustrating an exemplary system for measuring energy of natural gas according to some embodiments of the present disclosure.

FIG. 4 is a block diagram illustrating an exemplary system for measuring energy of natural gas according to some embodiments of the present disclosure; In some embodiments, the system for measuring energy of natural gas may be implemented on the processing device 140. In some embodiments, the system for measuring energy of natural gas 400 may include an obtaining module 410 and a determining module 420.

The obtaining module 410 may be configured to obtain carbon content and volume of the target natural gas supplied to use. The carbon content of the target natural gas refers to the mass of carbon elements in the target natural gas, and may include a mass ratio (for example, mass percentage) of the mass of carbon elements in the target natural gas to all elements of the target natural gas. A description of the related description of the carbon content and volume of the target natural gas can be found in operation 510, and details will not be described herein.

The determining module 420 may be configured to determine the first energy per unit volume of the target natural gas based on the carbon content of the target natural gas. The energy per unit volume of the target natural gas refers to the energy released by the unit volume of target natural gas combustion. In some embodiments, the energy per unit volume determined based on the carbon content of the target natural gas may be referred to as the first energy per unit volume. In some embodiments, the determining module 420 may determine the first prediction model through the first prediction model based on the ambient temperature and air oxygen content of the target natural gas when provided for use, the transmission rate of the target natural gas when provided, and the carbon content of the target natural gas energy per unit volume. Regarding the description of the determination of the first energy per unit volume, see the operation 520, and will not be described herein.

The determining module 420 may also be configured to determine the second energy per unit volume of the target natural gas based on the combustible component information of the target natural gas. In some embodiments, the energy per unit volume determined based on the combustible composition information of the target natural gas may be referred to as the second energy per unit volume. In some embodiments, the determining module 420 may determine the second natural gas through the second prediction model based on the ambient temperature and air oxygen content of the target natural gas when provided for use, the transmission rate of the target natural gas when provided, and the combustible composition information of the target natural gas energy per unit volume. For the relevant description of determining the energy per unit volume, reference may be made to the operation 530, and details are not repeated here.

The determining module 420 may also be configured to determine the difference between the first energy per unit volume and the second energy per unit volume. For the relevant description of determining the difference between the first energy per unit volume and the second energy per unit volume, reference may be made to operation 540, which will not be repeated here.

The determining module 420 may also determine whether the first energy per unit volume and the second energy per unit volume are accurate by the deviation determination model based on the difference between the first energy per unit volume and the second energy per unit volume. In some embodiments, the determining module 420 may be based on the ambient temperature and air oxygen content at which the target natural gas is provided for use (also referred to as ambient temperature and air oxygen content of the target natural gas when provided for use), the transmission rate at which the target natural gas is provided (also referred to as the transmission rate of the target natural gas when provided), and the difference between the first energy per unit volume and the second energy per unit volume to determine whether the first energy per unit volume and the second energy per unit volume are accurate through the deviation determination model. In some embodiments, the determining module 420 may determine a deviation coefficient by a deviation determination model based on a difference between the first energy per unit volume and the second energy per unit volume. For the relevant description of determining the deviation coefficient and whether the first energy per unit volume and the second energy per unit volume are accurate, reference may be made to operation 550, which will not be repeated here.

The determining module 430 may also be configured to determine the target natural gas energy. In some embodiments, in response to determining that the first energy per unit volume and the second energy per unit volume are accurate, the determining module 430 determines the target natural gas energy based on the first energy per unit volume, the second energy per unit volume, and volume. In some embodiments, in response to determining that the first energy per unit volume and the second energy per unit volume are inaccurate, determining module 430 may determine the target natural gas energy based on the first energy per unit volume, the second energy per unit volume, and the deviation coefficient. For the relevant description of determining the target natural gas energy, reference may be made to operations 560 and 570, which will not be repeated here.

The above description of the processing device 140 is for illustrative purposes only and is not intended to limit the scope of the present disclosure. For those skilled in the art, without departing from the principles of the present disclosure, various improvements and changes in form and detail can be made to the present disclosure of the above method and system. However, these changes and modifications do not deviate from the scope of the present disclosure. In some embodiments, the processing device 140 may include one or more other modules. Alternatively, one or more modules of the processing device 140 described above may be omitted. For example, the processing device 140 may include a storage module to store data generated by a module of processing device 140. In some embodiments, the module of the processing device 140 may be divided into two or more sub-modules.

Figure 5:
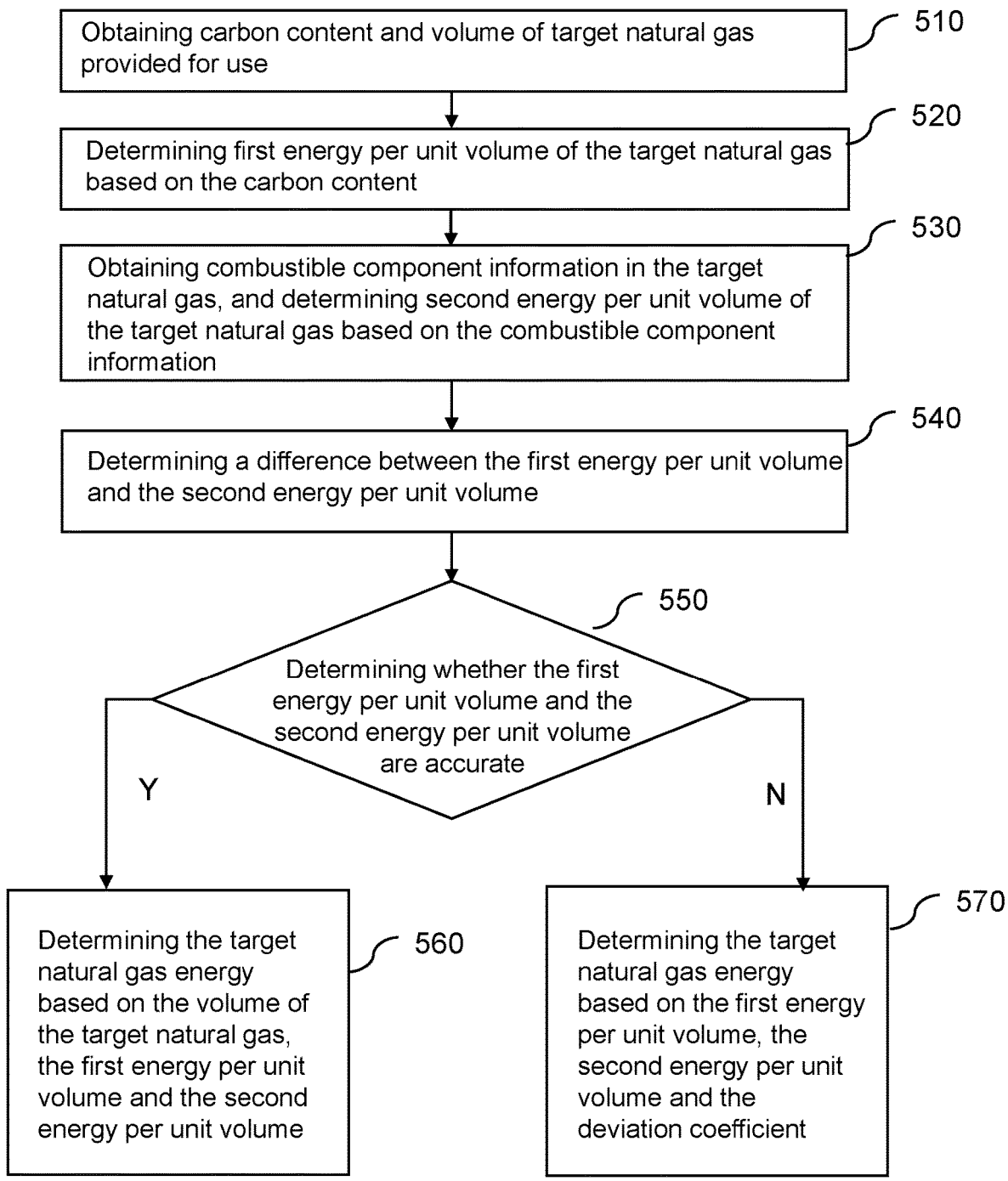
FIG. 5 is a flow diagram illustrating an exemplary process for measuring energy of natural gas according to some embodiments of the present disclosure.

FIG. 5 is a flow diagram illustrating an exemplary process for measuring energy of natural gas according to some embodiments of the present disclosure. In some embodiments, one or more operations of the process 500 shown in FIG. 5 may be implemented in scenario 100 shown in FIG. 1 or the computing device 200 shown in FIG. 2 or the mobile device 300 shown in FIG. 3. For example, the process 500 shown in FIG. 5 may be stored in a storage device (e.g., the storage device 150, the memory 220, the storage device 390) in the form of instructions and processed by a processing device (e.g., the processing device 140 shown in FIG. 1, the processor 210 of the computing device shown in FIG. 2 or the CPU 340 of the mobile device 300 shown in FIG. 3) invokes and/or executes.

In 510, the processing device (e.g., the processing device 140 shown in FIG. 1 or the processor 210 of the computing device shown in FIG. 2 or the CPU 340 of the mobile device 300 shown in FIG. 3) may obtain the carbon content and volume of the target natural gas when provided for use. In some embodiments, 510 may be performed by the obtaining module 410.

The carbon content of the target natural gas refers to the mass of carbon elements in the target natural gas and may include a mass ratio (for example, mass percentage) of the mass of carbon elements in the target natural gas to all elements of the target natural gas.

In some embodiments, the processing device may obtain the carbon content and volume of the target natural gas from one or more components or external devices in the application scenario 100. For example, the processing device may obtain the carbon content of the target natural gas from the carbon content detecting device 110-1 (e.g., chromatographic detector). For example, the processing device may obtain the volume of the target natural gas from the volume detecting device 110-2 (e.g., ultrasonic volume measuring instrument).

In 520, the processing device (e.g., the processing device shown in FIG. 1 or the processor 210 of the computing device shown in FIG. 2 or the CPU 340 of the mobile device 300 shown in FIG. 3) may, based on the carbon of the target natural gas content, determine the first energy per unit volume of the target natural gas. In some embodiments, 520 may be performed by determining module 420.

The energy per unit volume of the target natural gas refers to the energy released by the combusted target natural gas per unit volume. In some embodiments, the energy per unit volume determined based on the carbon content of the target natural gas can be referred to as the first energy per unit volume.

In some embodiments, the processing device may acquire the correspondence between the natural gas carbon content and the energy per unit volume. For example, the correspondence between the natural gas carbon content and the energy per unit volume may exist in a storage device (e.g., the storage device 150, the memory 220, the storage 390, or the external storage device). The processing device may retrieve the correspondence between natural gas carbon content and natural gas energy per unit volume from the storage device. In some embodiments, the processing device can further determine the first energy per unit volume based on the correspondence between the natural gas carbon content and the energy per unit volume. In some embodiments, the correspondence between the natural gas carbon content and the energy per unit volume can include a variety of natural gas carbon content ratings corresponding to the value of the energy per unit volume. For example, if the carbon content of the target natural gas is 60%, the processing device may determine the corresponding energy value per unit volume of natural gas when the carbon content of the natural gas is 60% according to the corresponding relationship between the carbon content of the natural gas and the energy per unit volume. The processing device may specify the energy value per unit volume as the first energy per unit volume of the target natural gas.

In some embodiments, the corresponding relationship (or correspondence) between the carbon content of natural gas and the energy per unit volume may be determined based on experience, the relationship between the carbon content of natural gas of historical natural gas and the energy per unit volume of historical natural gas burnt.

In some embodiments, the processing device may obtain the ambient temperature and air oxygen content at which the target natural gas is provided for use, and the transmission rate at which the target natural gas is provided. In some embodiments, target natural gas being provided may refer to target natural gas being delivered (e.g., target natural gas being delivered via a pipeline). In some embodiments, target natural gas being provided for use may refer to target natural gas being used for combustion (e.g., target natural gas being provided to residents for combustion).

The ambient temperature and air oxygen content of the target natural gas when provided for use refers to the ambient temperature and air oxygen content near a location where the target natural gas is delivered to and the target natural gas is used (e.g., the location of a residential residence). The transmission rate of the target natural gas when provided refers to a rate of the target natural gas transmitted in the gas pipeline.

In some embodiments, the processing device may obtain, from the application scenario 100 or an external device, the ambient temperature, air oxygen content, and transmission rate when the target natural gas is provided for use. For example, the processing device may acquire the ambient temperature, air oxygen content and transmission rate when the target natural gas is provided for use from a temperature sensor, an oxygen concentration sensor and a natural gas transmission rate sensor around the natural gas pipeline, respectively.

In some embodiments, the processing device may determine the first energy per unit volume by the first prediction model based on the ambient temperature at which the target natural gas is provided for use, the oxygen content of the air, the transmission rate, and the carbon content of the target natural gas. The first prediction model may be a model for determining energy per unit volume of the natural gas. By way of example only, the ambient temperature and air oxygen content at which the target natural gas is provided for use, the transmission rate at which the target natural gas is provided, the carbon content of the target natural gas may be input into a first prediction model, which may output a first energy per unit volume. In some embodiments, the first prediction model may include a deep learning model, such as a deep neural network (DNN) model, a convolutional neural network (CNN) model, a recurrent neural network (RNN) model, a feature pyramid network (FPN) model, or the like.

In some embodiments, the first prediction model may include a probabilistic prediction model (the probabilistic prediction model may include, for example, a DeepAR model, a DeepVAR model, a Transformer model, an LSTM, etc.). In some embodiments, the ambient temperature and air oxygen content at which the target natural gas is provided for use, the transmission rate at which the target natural gas is provided, and the carbon content of the target natural gas may be input into the first prediction model, and the first prediction model may output a plurality of predicted values of the first unit volume energy and a probability corresponding to each predicted value. In some embodiments, the predicted value with the highest probability among the multiple predicted values output by the first prediction model may be used as the first energy unit volume (also referred to as first unit volume energy) of the target natural gas.

In some embodiments, the processing device may obtain a first prediction model from one or more components (e.g., the network 120) from the application scenario 100 (e.g., the storage device 150, the terminal 130) or external device. For example, the first prediction model may be trained by a computing device (e.g., the processing device 140) and stored in a storage device (e.g., the storage device 150, the memory 220, and/or the storage 390) of the application scenario 100. The processing device may access the storage device and retrieve the first prediction model.

In some embodiments, the processing device may train the first prediction model based on at least one first training sample.

In some embodiments, the first prediction model may be trained according to the machine learning algorithm by a processing device or other computing device (e.g., a computing device of the first prediction model provider). The processing device may get at least one first training sample. Each first training sample may include a sample carbon content of the sample natural gas, a sample ambient temperature and a sample air oxygen content when the sample natural gas was provided for use, a sample transmission rate when the sample natural gas was provided, and a sample energy per unit volume of the sample natural gas value. The sample energy per unit volume may be marked as a sample energy true value of the sample natural gas by manual or processing device. In some embodiments, the sample energy per unit volume value may be determined by the actual combustion of the sample natural gas. For example, the processing device may specify the actual energy value of the actual combustion of the sample natural gas as the sample energy per unit volume value.

The training of the first prediction model may include one or more first iterations, and each first iteration may include updating model parameters of the first prediction model based on the first training samples. In some embodiments, the optimization target of the first prediction model training may include adjusting the model parameters such that the value of the first loss function becomes smaller (e.g., minimizing the value of the first loss function). The first loss function may be used to characterize the difference between the first energy per unit volume value and the sample energy per unit volume value predicted. Exemplary, the first loss function may include focus loss functions, logarithmic loss functions, cross-entropy loss, or the like. For example, the sample carbon content, sample transmission rate, sample ambient temperature, and sample air oxygen content in each first training sample may be input into the first prediction model, and the first prediction model may output predictive value of the first unit volume energy of the training sample. The first loss function may be used to characterize the difference between the first energy per unit volume predicted value of the first training sample and the sample energy per unit volume value. In some embodiments, the optimization target of the first predicted model training may also include maximizing the probability of maximizing the plurality of predicted values of the first prediction model output.

In some embodiments, when the first prediction model satisfies the first termination condition in a certain first iteration, the training can be stopped. Exemplarily, the first termination condition may include any one or a combination of the following: the value of the first loss function obtained in a certain iteration is less than a threshold, a certain number of iterations have been performed, the first loss function has converged (For example, the difference between the value of the loss function obtained in the previous iteration and the value of the loss function obtained in this iteration is within a preset threshold), among the multiple predicted values output by the first prediction model, the probability corresponding to the sample energy value per unit volume exceeds a preset threshold or the like. In some embodiments, when iteration does not satisfy the first termination condition, the processing device may further update the first prediction model for the next iteration according to a preset algorithm (e.g., a reverse propagation algorithm). If the first termination condition is satisfied in the current iteration, the processing device may complete the training of the first prediction model.

In 530, the processing device (e.g., the processing device 140 shown in FIG. 1 or the processor 210 of the computing device shown in FIG. 2 or the CPU 340 of the mobile device 300 shown in FIG. 3) may obtain the combustible composition information of the target natural gas, and based on the combustible composition information, determine the second energy per unit volume of the target natural gas. In some embodiments, 530 may be performed by the determining module 420.

In some embodiments, the energy per unit volume of the target natural gas determined based on the target natural gas may be referred to as the second energy per unit volume.

The combustible component of the target natural gas refers to a compound that may be combustible in the target natural gas. For example, the combustible components of the target natural gas may include methane, ethane, or the like.

The combustible component information refers to information related to one or more combustible component. In some embodiments, the combustible component information of the target natural gas may include various combustible components and their content included in the target natural gas. In some embodiments, the content of the combustible component may be represented by volume fraction or mass fraction. For example, if the combustible components of the target natural gas include methane, the volume of which is 2 L, and the volume of the target natural gas is 10 L, the volume fraction of methane in the target natural gas is 20%.

In some embodiments, the processing device may apply the scenario 100 or obtain information on various components contained in the target natural gas (e.g., types and contents of the various components) from an external device. For example, the external device (e.g., a gas chromatograph) may analyze the target natural gas to acquire a variety of ingredient information contained in the target natural gas. The processing device may obtain the combustible component information of the target natural gas from a variety of ingredient information contained in the target natural gas.

In some embodiments, the processing device may obtain a correspondence between the combustible component information and the energy per unit volume in natural gas. For example, the correspondence between the natural gas combustible component information and the energy per unit volume may exist in a storage device (e.g., the storage device 150, the memory 220, the storage 390, or the external storage device). The processing device may retrieve the correspondence between natural gas combustible component information and natural gas energy per unit volume from the storage device. In some embodiments, the correspondence between the combustible component information of natural gas and the energy per unit volume may include values of energy per unit volume corresponding to the values of the combustible component information of various natural gas. In some embodiments, the processing device may further determine the second energy per unit volume based on the correspondence between the natural gas combustible component information and the energy per unit volume. For example, the combustible components in the target natural gas include methane and ethane, with 20% methane and 60% ethane. The processing device may determine the energy value per unit volume n1 of methane and the energy value per unit volume n2 of ethane according to the correspondence between the combustible component information of the natural gas and the energy per unit volume. The processing device may determine that the second energy per unit volume is n1*20%+n2*60%.

In some embodiments, the corresponding relationship between the combustible composition information of natural gas and the unit volume energy (also referred to as energy per unit volume) may be determined according to experience, the relationship between the historical natural gas combustible composition information and the unit volume energy of historical natural gas burning.

In some embodiments, the processing device may obtain the ambient temperature and air oxygen content when the target natural gas is provided for use, and the transmission rate of the target natural gas when being provided. In some embodiments, the processing device may determine the second energy per unit volume through a second prediction model based on ambient temperature, air oxygen content, transmission rate, and combustible composition information. For the acquisition of ambient temperature, air oxygen content, and obtaining the transmission rate, please refer to operation 520, and details are not described herein again.

In some embodiments, the second prediction model may be a model for determining the second energy per unit volume. By way of example only, the ambient temperature and air oxygen content when the target natural gas is provided for use, the transmission rate when the target natural gas is provided, the combustible composition information of the target natural gas may be input into the second prediction model, and the second prediction model may output the second energy per unit volume. In some embodiments, the model structure of the second prediction model may be the same or similar to the model structure of the first prediction model. In some embodiments, the processing device may obtain the second prediction model in a manner similar to acquiring the first prediction model, and the related description will be described in operation 520, and details are not described herein again.

In some embodiments, the second prediction model may include a probability prediction model (probably prediction model may include, for example, a DeepAR model, a DeepVAR model, a Transformer model, an LSTM model, etc.) In some embodiments, the ambient temperature and air oxygen content at which the target natural gas is provided for use, the transmission rate at which the target natural gas is provided, and the carbon content of the target natural gas may be input into the second prediction model, which may output a plurality of predicted values of energy per unit volume and the corresponding probability for each predicted value. In some embodiments, the predicted value with the highest probability among a plurality predicted values output by the second prediction model may be used as the second energy per unit volume of the target natural gas.

In some embodiments, the processing device may obtain at least one second training sample. Each second training sample may include sample combustible composition information of the sample natural gas, sample ambient temperature and sample air oxygen content when the sample natural gas was provided for use, sample transmission rate when the sample natural gas was provided, and the sample energy value per unit volume of the sample natural gas. The sample energy per unit volume may be marked as a sample energy per unit volume true value of the sample natural gas by manual or the processing device. In some embodiments, the sample energy per unit volume true value is determined by the actual combustion of the sample natural gas.

In some embodiments, the processing device may train the second prediction model based on one or more second training samples to acquire a second prediction model after training. The training of the second prediction model may include one or more second iterations, and each of the second iterations may include updating model parameters of the second prediction model based on the second training sample. In some embodiments, the optimization target of the second prediction model may include adjusting the model parameters such that the value of the second loss function becomes smaller (e.g., minimizing the value of the second loss function). The second loss function may be used to characterize the difference between the second energy per unit volume value predicted by the second prediction model and the sample energy per unit volume value. Exemplary, the second loss function may include focus loss functions, logarithmic loss functions, cross-entropy loss, or the like. For example, the sample combustible composition information, sample transmission rate, sample ambient temperature, and sample air oxygen content in each second training sample can be input into the second prediction model, which may output a predicted second energy value per unit volume for the training sample. The second loss function may be used to characterize the difference between the predictive (or predicted) second energy per unit volume and the sample energy per unit volume of the second training sample. In some embodiments, the optimization target of the second prediction model training may further comprise the probability of maximizing the sample energy per unit volume value in a plurality of predicted values output by the second prediction model.

In some embodiments, if the second prediction model satisfies the second termination condition in a certain second iteration, the training can be stopped. Exemplarily, the second termination condition may include any one or a combination of the following: the value of the second loss function obtained in a certain iteration is less than a threshold, a certain number of iterations have been performed, the second loss function has converged, among the multiple predicted values output by the second prediction model, the probability corresponding to the energy value per unit volume of the sample exceeds a preset threshold, or the like. In some embodiments, the processing device may further update the second prediction model for the next iteration when the iteration does not satisfy the second termination condition (for example, a reverse propagation algorithm). If the second termination condition is satisfied in the current iteration, the processing device may complete the training of the second prediction model.

In 540, the processing device (e.g., the processor 210 of the processing device 140 shown in FIG. 1, the processor 210 shown in the calculating device shown in FIG. 2, the CPU 340 shown in the mobile device 300 shown in FIG. 3.) may determine a difference between the first energy per unit volume and the second energy per unit volume. In some embodiments, 540 may be performed by the determining module 420.

In some embodiments, the processing device may designate a value of the first unit volume energy minus the second unit volume energy as the difference between the first unit volume energy and the second unit volume energy. Alternatively, the processing device may designate a value obtained by subtracting the first unit volume energy from the second unit volume energy as the difference between the first unit volume energy and the second unit volume energy.

In 550, the processing device (e.g., the processing device 140 shown in FIG. 1 or the processor 210 of the computing device shown in FIG. 2 or the CPU 340 of the mobile device 300 shown in FIG. 3) may, based on the difference between the first energy per unit volume and the second energy per unit volume, determine whether the first unit volume energy and the second unit volume energy are accurate through a deviation determination model. In some embodiments, 550 may be performed by the determining module 420.

The deviation determination model may be a model for determining whether there is a deviation between different energy per unit volume values. In some embodiments, the input of the deviation determination model may include the difference between the first energy per unit volume and the second energy per unit volume. The output of the deviation determination model may include determination results and/or related information whether the first energy per unit volume and the second energy per unit volume are accurate (e.g., deviation coefficients of the first and second energy per unit volume), or the like.

In some embodiments, the processing device may obtain the ambient temperature and air oxygen content at which the target natural gas is provided for use, and the transmission rate at which the target natural gas is provided. The processing device may determine the first energy per unit volume through the deviation determination model based on the ambient temperature at which the target natural gas is provided for use, the air oxygen content and transmission rate, and the difference between the first energy per unit volume and the second energy per unit volume and whether the first energy per unit volume and the second unit volume energy are accurate.

For example, the processing device may input the ambient temperature, air oxygen content and transmission rate, and the difference between the first unit volume energy and the second unit volume energy provided for use into the deviation determination model. The deviation determination model may output a determination result of whether the first unit volume energy and the second unit volume energy are accurate. In some embodiments, the deviation determination model may also output other information (e.g., the deviation coefficient of the first energy per unit volume and the second energy per unit volume). For example, the deviation coefficient may reflect the degree of deviation between the first energy per unit volume and the second energy per unit volume. For example, the deviation coefficient is 0.2, indicating that the degree of deviation between the first energy per unit volume and the second energy per unit volume is 20%. In some embodiments, the larger the deviation coefficient between the first energy per unit volume and the second energy per unit volume, the higher the degree of deviation between the first energy per unit volume and the second energy per unit volume, that is, the accuracy of the first unit volume energy and the second unit volume energy is lower. In some embodiments, when the deviation determination model outputs determination results of the accurate first energy per unit volume and the second energy per unit volume, the corresponding deviation coefficient may be 0 or less than a deviation threshold (e.g., 0.08, 0.1). When the deviation determination model outputs an determination result that the first unit volume energy and the second unit volume energy are inaccurate, the deviation coefficient may be simultaneously output. In some embodiments, the model structure of the deviation determination model may be the same or similar to the first prediction model.

In some embodiments, the processing device may obtain a deviation determination model similar to acquiring the first prediction model, and the relevant description is explained in operation 520, and details are not described herein again.

According to some embodiments of the present disclosure, the processing device may, based on ambient temperature, air oxygen content, transmission rate, and the difference between the first energy per unit volume and the second energy per unit volume when the target natural gas is being used, determine whether the first energy per unit volume and the second energy per unit volume are accurate. In this way, the influence of different conditions on the volume energy of the target natural gas can be considered at the same time, which can ensure the accuracy of the determination results of whether the acquired first energy per unit volume and the second energy per unit volume are accurate, and then ensures the accuracy of the target natural gas energy subsequently determined based on the determination results of whether the first energy per unit volume and the second energy per unit volume are accurate.

In some embodiments, the processing device may acquire one or more third training samples. Each third training sample may include the difference between the sample first energy per unit volume and the sample second energy per unit volume of the sample natural gas, the sample ambient temperature and the sample air oxygen content when the sample natural gas was provided for use, the transmission rate of the target natural gas when provided, and the sample energy value per unit volume of the sample natural gas, etc. In some embodiments, the sample first energy per unit volume can be determined by the method of determining the first energy per unit volume similar to operation 520, and the related description will be described in connection with the description. In some embodiments, the sample second energy per unit volume can be determined similar to operation 530 of the determination of the second energy per unit volume, and the related description please refer to operation 530, which will not be repeated here. In some embodiments, the sample energy per unit volume value can be determined by the actual combustion of the sample natural gas. For example, the processing device can obtain the energy per unit volume of the actual combustion of the sample natural gas. The processing device can specify the energy per unit volume of the actual combustion of sample natural gas as the sample energy per unit volume value.

In some embodiments, each of the third training samples (i.e., the true value of the predicted result of whether the sample first energy per unit volume and the second energy per unit volume are accurate) can be determined by manual labeling or automatic labeling. In some embodiments, the processing device can determine the predictive sample energy per unit volume of sample natural gas based on sample first energy per unit volume and sample second energy per unit volume. The processing device may determine the difference between the predictive sample energy per unit volume and the sample energy per unit volume. The processing device may compare the difference between the predictive sample energy per unit volume and the sample energy per unit volume to determine the label of the training sample. If the difference between the predictive sample energy per unit volume and the sample energy per unit volume is greater than the preset threshold, the label of the training sample may be that the sample first energy per unit volume and the second energy per unit volume are inaccurate. If the difference between the predictive sample energy per unit volume and the sample energy per unit volume is less than or equal to the preset threshold, the label of the training sample may be that the sample first energy per unit volume and the sample second energy per unit volume are accurate. In some embodiments, the processing device determines the corresponding sample deviation coefficient according to the difference between the predicted sample energy per unit volume and the sample energy per unit volume. For example, the processing device may determine the ratio of the difference between the predictive sample energy per unit volume and the sample energy per unit volume to the sample energy per unit volume is the sample deviation coefficient.

In some embodiments, the processing device may obtain a well-trained deviation determination model based on one or more third training samples, the training deviation determination model. The training of the deviation determination model may include one or more third iterations, in each of the third iterations, may include model parameters based on a third training sample update deviation determination model. In some embodiments, the deviation determination model training can include adjusting the model parameters such that the value of the third loss function becomes smaller (e.g., minimizing the value of the third loss function). The third loss function may be used to characterize a difference between the predicted result whether of the sample first energy per unit volume and the sample second energy per unit volume are accurate output by the deviation determination model and the label of the sample. Exemplary, third loss functions may include focus loss functions, logarithmic loss functions, cross entropy loss, or the like. For example, the sample transmission rate in each third training sample, the difference between the sample first energy per unit volume and the sample second energy per unit volume, the ambient temperature of the sample, and the oxygen content of the sample air may be input into the deviation determination model, the deviation determination model can output a prediction result of whether the sample first energy unit volume and the sample second energy unit volume of the training sample are accurate. The third loss function may be used to represent the difference between the prediction result of whether the sample first energy unit volume and the sample second energy unit volume of the third training sample are accurate and the sample label.

In some embodiments, the deviation determination model satisfies the third termination condition in a certain third iteration, and the training can be stopped. Exemplarily, the third termination condition may include any one or a combination of the following: the value of the third loss function obtained in a certain iteration is less than a threshold, a certain number of iterations have been performed, the third loss function has converged, etc. In some embodiments, when the iteration does not satisfy the third termination condition, the processing device may further update the deviation determination model for the next iteration according to a preset algorithm (e.g., a backpropagation algorithm). If the third termination condition is satisfied in the current iteration, the processing device may complete the training of the deviation determination model.

In some embodiments, the processing device can perform operation 560 in response to determining that the first energy per unit volume and the second energy per unit volume are accurate. In response to determining that the first energy per unit volume and the second energy per unit volume are not accurate, the processing device may perform operation 570.

In 560, the processing device (e.g., the processing device 140 shown in FIG. 1 or the processor 210 of the computing device shown in FIG. 2 or the CPU 340 of the mobile device 300 shown in FIG. 3) may determine the energy of the target natural gas based on the volume of the target natural gas, the first unit volume energy and the second unit volume energy. In some embodiments, 560 may be performed by the determining module 420.

The target natural gas energy (also referred to as energy of the target natural gas) may refer to the energy released when the target natural gas is burned.

In some embodiments, the processing device may determine the average of the first energy per unit volume and the second energy per unit volume. In some embodiments, the processing device may determine the product of the average value of the first unit volume energy and the second unit volume energy and the volume of the target natural gas as the target natural gas energy. In some embodiments, the processing device may acquire a first weight corresponding to the first energy per unit volume and a second weight corresponding to the second energy per unit volume. The processing device may perform weighted sum of the first energy per unit volume and the second energy per unit volume to acquire the energy per unit volume of the target natural gas. The processing device may determine the product of the unit volume energy of the target natural gas and the volume of the target natural gas as the target natural gas energy. For example, if the first energy per unit volume is A, the first weight is m1, the second energy per unit volume is B, and the second weight m2, the processing device 140 may determine the energy per unit volume of the target natural gas as (Am1+Bm2).

In some embodiments, the first weight and second weight may be set by the user according to the experience, or may be set by the processing device according to the default value or actual needs of the application scene 100. In some embodiments, the processing device may determine the first weight based on the output of the first prediction model, and the second weight may be determined based on the output of the second prediction model. For example, the processing device may acquire the first probability a corresponding to the first unit volume energy output by the first prediction model and a second probability b corresponding to the second unit volume energy output by the second prediction model. The processing device may determine the first weight is a/(a+b), the second weight is b/(a+b).

In 570, the processing device (e.g., the processing device 140 shown in FIG. 1 or the processor 210 of the computing device shown in FIG. 2 or the CPU 340 of the mobile device 300 shown in FIG. 3) may determine the energy of the target natural gas based on the first energy per unit volume, the second energy per unit volume and the deviation coefficient. In some embodiments, 570 may be executed by determining module 420

In some embodiments, the processing device may obtain the calibrated energy per unit volume by the correction model. The correction model may be a model for correcting the first energy per unit volume and the second energy per unit volume. For example, the processing device may input the first energy per unit volume, the second energy per unit volume, and the deviation coefficient, and the correction model may output the corrected energy per unit volume. In some embodiments, the correction model may include a depth learning model such as a depth neural network (DNN) model, convolutional neural network (CNN) model, or the like. In some embodiments, the processing device may obtain the correction model similar to acquiring a first prediction model, and the related description see the operation 520, hereby not described herein.

In some embodiments, the processing device may obtain one or more fourth training samples. Each fourth training sample may include the sample first unit volume energy of the natural gas, the sample second unit volume energy, the sample deviation coefficient corresponding to the sample natural gas, the sample unit volume energy of the sample natural gas, or the like. The sample energy per unit volume may be marked as a sample energy true value of the sample natural gas by manual or processing device. The sample deviation coefficient means the deviation coefficient of the first energy per unit volume and the sample second energy per unit volume. In some embodiments, the first unit volume energy of the sample may be determined in a manner similar to the method for determining the first unit volume energy described in operation 520. For related descriptions, please refer to operation 520, which will not be repeated here. In some embodiments, the second energy per unit volume of the sample may be determined in a manner similar to the method for determining the energy per unit volume of the sample described in operation 530. For the relevant description, please refer to operation 530, which will not be repeated here. In some embodiments, the determination of the sample deviation coefficient may be similar to the determination of the deviation coefficient of the first energy per unit volume and the second energy per unit volume. In some embodiments, the sample energy per unit volume value may be determined by the actual combustion of the sample natural gas. For example, the processing device may specify the actual energy value of the actual combustion of the sample natural gas as the sample energy per unit volume value.

In some embodiments, the processing may be trained based on one or more fourth training samples, and the correction model is trained. The training of the correction model may include one or more fourth iterations, in each of the fourth iterations, can include model parameters based on the fourth training sample update correction model. In some embodiments, the optimization target of the correction model training may include adjusting the model parameters such that the value of the fourth loss function becomes smaller (e.g., minimizing the value of the fourth loss function). The fourth loss function may be used to characterize the difference between the energy per unit volume value predicted by the correction model and the sample energy per unit volume value. Exemplary, the fourth loss function may include focus loss functions, logarithmic loss functions, cross-entropy loss, and so on. For example, the sample first unit volume energy, the sample second unit volume energy, and the sample deviation coefficient in each fourth training sample may be input into the correction model, and the correction model may output the predicted energy per unit volume value of the sample. The fourth loss function may be used to characterize the difference between predicted energy per unit volume value and the sample energy per unit volume value of the fourth training sample.

In some embodiments, if the correction model satisfies the fourth termination condition in a certain fourth iteration, the training may be stopped. Exemplarily, the fourth termination condition may include any one or a combination of the following: the value of the fourth loss function obtained in a certain iteration is less than a threshold, a certain number of iterations have been performed, the fourth loss function has converged, etc. In some embodiments, when iteration does not satisfy the fourth termination condition, the processing device can further update the correction model for the next iteration according to a preset algorithm (e.g., a reverse propagation algorithm). If the fourth termination condition is satisfied in the current iteration, the processing device may complete the training of the correction model.

In some embodiments, the processing device may determine the target natural gas energy based on the calibrated energy per unit volume. For example, the processing device may determine the product of the calibrated energy per unit volume and the volume of the target natural gas as the target natural gas energy.

According to some embodiments of the present disclosure, the processing device may determine whether the first energy per unit volume and the second energy per unit volume are accurate by the deviation determination model. When determining that the first energy per unit volume and the second energy per unit volume are accurate, the processing device may determine the target natural gas energy based on the first energy per unit volume and the second energy per unit volume, thereby ensuring the accuracy of the target natural gas energy. When determining that the first energy per unit volume and the second energy per unit volume are inaccurate, the processing device may obtain the corrected energy per unit volume through the correction model based on the first energy per unit volume, the second energy per unit volume and the deviation coefficient. The processing device may further determine the energy of the target natural gas based on the calibrated energy per unit volume, thereby ensuring the accuracy of the target natural gas energy.

Figure 6:
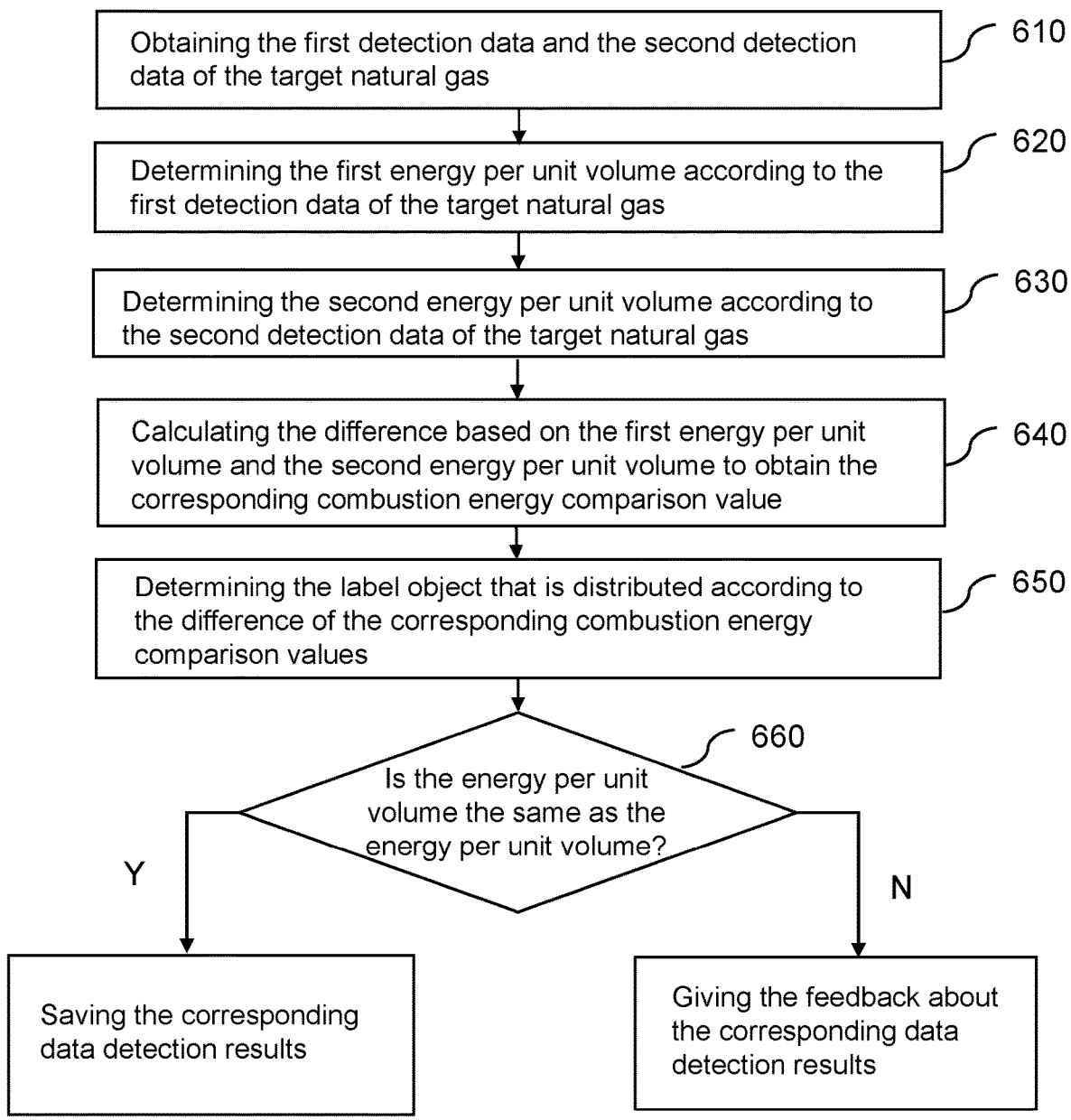
FIG. 6 is a flow diagram illustrating an exemplary process for measuring energy of natural gas according to some embodiments of the present disclosure.

FIG. 6 is a flow diagram illustrating an exemplary process for measuring energy of natural gas according to some embodiments of the present disclosure. In some embodiments, one or more operations of the process 600 shown in FIG. 6 may be implemented in scenario 100 shown in FIG. 1 or the computing device 200 shown in FIG. 2 or the mobile device 300 shown in FIG. 3. For example, the process 600 shown in FIG. 6 may be stored in a storage device (e.g., the storage device 150, the memory 220, the storage device 390) in the form of instructions and processed by a processing device (e.g., the processing device 140 shown in FIG. 1) or the processor 210 of the computing device shown in FIG. 2 or the CPU 340 of the mobile device 300 shown in FIG. 3) invoked and/or executed.

In 610, the processing device may obtain the first detection data and the second detection data of the target natural gas.

In some embodiments, the target natural gas may be input into the chromatographic detector, and the chromatographic detector may label the carbon element to obtain the first detection data.

In some embodiments, the target natural gas may be input to the ultrasonic detector to perform volume detection to obtain a second detection data.

In 620, the processing device may determine the first energy per unit volume according to the first detection data of the target natural gas.

In some embodiments, the processing device may extract the carbon element characteristics corresponding to the carbon element in the first detection data. The processing apparatus may analyze the carbon element characteristics to obtain a corresponding carbonaceous material set. The processing device may also extract the preset combustible material set in the first preset database, map the carbon-containing material set to the preset combustible material set, obtain the substances matching the preset combustible material set, and delete the unmatched substances. The processing device may also calculate the percentage of carbon content according to the matching substance to obtain a corresponding carbon content. The processing device may further extract the carbon element energy release coefficient in the preset database, and obtain the first unit volume energy based on the carbon content and the carbon element energy release coefficient of the target natural gas.

In 630, the processing device may determine the second energy per unit volume value according to the second detection data of the target natural gas. In some embodiments, the processing device may obtain the volume and second detection data of the target natural gas. The processing device may perform feature extraction on the combustible components in the target natural gas based on the volume of the target natural gas and the second detection data, so as to obtain the combustible gas component characteristics of the target natural gas. The combustible gas composition feature may be used to describe the combustible composition ratio feature of the target natural gas.

The processing device may take advantage of the characteristic extraction of the combustible component based on the volume and second detection data of the target natural gas to obtain the characteristics of the target natural gas. The combustible component features may be used to describe the combustion state of the target natural gas. In some embodiments, when the target natural gas includes at least two groups of input gases, for each group of input gases in the target natural gas, the processing device performs a binarization operation on the combustible gas composition feature and the combustible composition feature of the input gas, respectively, to obtain the result of the binarization operation. The processing device may find the first preset database based on the binarization operation result to obtain the initial lookup results.

For each of the combustible gases included in the initial lookup results, the processing apparatus can obtain the average similarity and match between the input gas and the combustible gas in the target natural gas. The processing device may combine the initial lookup results of each set of input gas matching results based on the average similarity and matching degree matching each of the combustible gases, resulting in a target combustible gas that matches the target natural gas; and energy calculation is performed based on the target combustible gas that matches the target natural gas, resulting in the corresponding second energy per unit volume.

In 640, the processing device may calculate the difference based on the first energy per unit volume and the second energy per unit volume to obtain a combustion energy comparison value.

In 650, the processing device may determine the label object based on the combustion energy comparison value. In some embodiments, the label object includes a label object determined based on numeric characteristics, and/or the label object includes a label object determined based on a historical combustion record.

In some embodiments, the processing device may determine the corresponding real-time combustion data difference value based on the difference distribution of the combustion energy comparison value. The processing device may calculate the calculation of the oxygen consumption based on real-time combustion data difference, resulting in a corresponding oxygen consumption value. The processing device may also calculate the oxygen consumption on the average combustion released energy value based on the historical combustion records, and obtain the historical average oxygen consumption value The processing device may further obtain the corresponding data deviation range by the oxygen consumption value and the historical average oxygen permeability value.

For example, the processing device may acquire historical energy release values that contain multiple combustions, and at least three groups contain multiple combustion reference data values, wherein the reference data value and the historical energy release value have different combustion scenarios. The processing device may extract historical energy release values of the preset area from the historical energy release value, and extract the reference data value box for the preset area from the reference data value. The historical energy release value block includes a plurality of combustion energy points for marking the combustion information corresponding to the combustion material in the historical energy release value. The reference data value frame includes a plurality of reference energy points for marking the combustion information corresponding to the combustion material in the reference data value. The processing device may map multiple combustion energy points to the reference data value according to the preset coordinate axis conversion formula to obtain a plurality of mapping points. The processing device may construct a point-in-one conversion formula between multiple mapping points and multiple reference energy points. The processing device may also obtain the data deviation range of the reference energy point corresponding to the combustion energy point in the historical energy release value in the reference data value based on the point-to-point conversion formula.

In 660, the processing device may compare and display the auxiliary prompt data of the label object during the energy release process of the corresponding combustion energy comparison value, and obtain a result of whether the first unit volume energy and the second unit volume energy are consistent. In some embodiments, the result of whether the first unit volume energy and the second unit volume energy are consistent can be used to characterize whether the carbon element released energy corresponding to the first detection data and the second detection data is consistent.

In some embodiments, the processing device may obtain an error interval range model corresponding to the comparison value of the combustion energy according to the data deviation range in the label object. The processing device may input the combustion energy comparison value into the deviation interval range model, and if the first unit volume energy is consistent with the second unit volume energy, the corresponding data detection result is saved. If the first energy per unit volume and the second energy per unit volume are inconsistent, the corresponding data detection result feedback will be given.

Having thus described the basic concepts, it may be rather apparent to those skilled in the art after reading this detailed disclosure that the foregoing detailed disclosure is intended to be presented by way of example only and is not limiting. Although Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation. That may all generally be referred to herein as a "module," "unit," "component," "device," or "system." Furthermore, aspects of the present disclosure may take the form of a computer program product embodied in one or more computer-readable media having computer-readable program code embodied thereon.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A method for measuring energy of natural gas based on a reduced data deviation, implemented on a computing device comprising at least one storage device and at least one processor, wherein the at least one processor processes data and/or information obtained from a metering device of natural gas and/or the at least one storage device; wherein the metering device of natural gas is configured to collect data related to natural gas; wherein the metering device of natural gas includes a carbon content detecting device and a volume detecting device; wherein the carbon content detecting device includes a chromatographic detector, and the volume detecting device includes a ultrasonic volume measuring instrument; wherein the carbon content detecting device is configured to obtain a carbon content of natural gas, and the volume detecting device is configured to obtain a volume of natural gas, the method comprising:
obtaining, by the carbon content detecting device, a carbon content of target natural gas when provided for use, and obtaining, by the volume detecting device, a volume of the target natural gas when provided for use;
determining first energy per unit volume of the target natural gas based on the carbon content, wherein the determining first energy per unit volume of the target natural gas based on the carbon content includes:
extracting a carbon element energy release coefficient in a first preset database, and obtaining the first energy per unit volume based on the carbon content and the carbon element energy release coefficient;
obtaining combustible component information of the target natural gas, and determining second energy per unit volume of the target natural gas based on the combustible component information;
determining a difference between the first energy per unit volume and the second energy per unit volume;
based on the difference between the first energy per unit volume and the second energy per unit volume, determining whether the first energy per unit volume and the second energy per unit volume are accurate by a deviation determination model, wherein the deviation determination model is a model for determining whether there is a deviation between different energy per unit volume, and a training process of the deviation determination model comprises:
obtaining at least one first training sample, wherein each of the at least one first training sample includes a difference between the sample first energy per unit volume and the sample second energy per unit volume of the sample natural gas, a sample ambient temperature and a sample air oxygen content of the sample natural gas when provided for use, a sample transmission rate of the sample natural gas when provided, and a sample energy per unit volume value of the sample natural gas, wherein the sample energy per unit volume value is determined by an actual combustion of the sample natural gas;
determining predictive sample energy per unit volume of the sample natural gas based on the sample first energy per unit volume and the sample second energy per unit volume; determining a difference between the predictive sample energy per unit volume and the sample energy per unit volume; determining a label of the first training sample by comparing the difference between the predictive sample energy per unit volume and the sample energy per unit volume; wherein if the difference between the predictive sample energy per unit volume and the sample energy per unit volume is greater than a preset threshold, the label of the first training sample is that the sample first energy per unit volume and the sample second energy per unit volume are inaccurate; if the difference between the predictive sample energy per unit volume and the sample energy per unit volume is less than or equal to the preset threshold, the label of the first training sample is that the sample first energy per unit volume and the sample second energy per unit volume are accurate; and
obtaining the deviation determination model by training an initial deviation determination model based on the at least one first training sample, wherein a training of the initial deviation determination model includes one or more third iterations, each of the one or more third iterations includes updating model parameters of the initial deviation determination model based on the at least one first training sample such that a value of a third loss function is smaller; wherein the third loss function is used to characterize a difference between a predicted result of whether the sample first energy per unit volume and the sample second energy per unit volume are accurate, which is output by the initial deviation determination model, and the label of the first training sample; stopping training when the initial deviation determination model satisfies a third termination condition in a certain third iteration; and
in response to determining that the first energy per unit volume and the second energy per unit volume are accurate, determining energy of the target natural gas based on the first energy per unit volume, the second energy per unit volume, and the volume of the target natural gas.

2. The method of claim 1, wherein the metering device of natural gas further includes a temperature monitoring device, an oxygen concentration monitoring device, a natural gas transmission rate monitoring device, which are arranged on a natural gas pipeline or around the natural gas pipeline, the determining, based on the carbon content, the first energy per unit volume of the target natural gas comprises:
obtaining, by the temperature monitoring device, an ambient temperature of the target natural gas when provided for use, obtaining, by the oxygen concentration monitoring device, an air oxygen content of the target natural gas when provided for use, and obtaining, by the natural gas transmission rate monitor, a transmission rate of the target natural gas when provided; and
determining the first energy per unit volume by a first prediction model based on the ambient temperature, the air oxygen content, the transmission rate, and the carbon content.

3. The method of claim 2, wherein a training process of the first prediction model comprises:
obtaining at least one second training sample, wherein each of the at least one second training sample includes a sample carbon content of the sample natural gas, the sample ambient temperature and the sample air oxygen content of the sample natural gas when provided for use, the sample transmission rate of the sample natural gas when provided and the sample energy per unit volume value of the sample natural gas, wherein the sample energy per unit volume value is determined by the actual combustion of the sample natural gas, wherein the at least one processor specifies an energy per unit volume value of the actual combustion of the sample natural gas as the sample energy per unit volume value; and
obtaining the first prediction model by training an initial first prediction model based on the at least one second training sample, wherein a training of the first prediction model includes one or more first iterations, and each first iteration includes updating model parameters of the initial first prediction model based on the second training sample such that a value of a first loss function is smaller; wherein the first loss function is used to characterize a difference between the first energy per unit volume predicted by the initial first prediction model and the sample energy per unit volume; stopping training when the initial first prediction model satisfies a first termination condition in a certain first iteration; wherein the first termination condition includes at least one of the value of the first loss function less than a threshold, performing a certain number of iterations, the first loss function converges, a probability corresponding to the sample energy per unit volume value exceeding a preset probability threshold among predicted values output by the initial first prediction model.

4. The method of claim 2, further comprising:

determining the first energy per unit volume and a first probability corresponding to the first energy per unit volume by the first prediction model based on the ambient temperature, the air oxygen content, the transmission rate and the carbon content;

determining the second unit volume energy and a second probability corresponding to the second energy per unit volume by the second prediction model based on the ambient temperature, the air oxygen content, the transmission rate, and the combustible component information;

the determining of the energy of the target natural gas based on the first energy per unit volume, the second energy per unit volume and the volume comprises:

determining a first weight corresponding to the first energy per unit volume based on the first probability;

determining a second weight corresponding to the second energy per unit volume based on the second probability; and determining the energy of the target natural gas based on the first energy per unit volume, the first weight, the second energy per unit volume, the second weight, and the volume.

5. The method of claim 1, wherein the determining the second energy per unit volume of the target natural gas based on the combustible component information comprises:

obtaining an ambient temperature and air oxygen content of the target natural gas when provided for use, and a transmission rate of the target natural gas when provided; and determining the second energy per unit volume by a second prediction model based on the ambient temperature, the air oxygen content, the transmission rate, and the combustible component information.

6. The method of claim 5, wherein a training process of the second prediction model comprises:

obtaining at least one third training sample, wherein each of the at least one third training sample includes a sample combustible component information of the sample natural gas, the sample ambient temperature and the sample air oxygen content of the sample natural gas when provided for use, the sample transmission rate of the sample natural gas when provided and the sample energy per unit volume value of the sample natural gas, wherein the sample energy per unit volume value is determined by the actual combustion of the sample natural gas, wherein the at least one processor specifies an energy per unit volume value of the actual combustion of the sample natural gas as the sample energy per unit volume value; and obtaining the second prediction model by training an initial second prediction model based on the at least one third training sample, wherein a training of the second prediction model includes one or more second iterations, and each second iteration includes updating model parameters of the initial second prediction model based on the third training sample such that a value of a second loss function is smaller; wherein the second loss function is used to characterize a difference between the second energy per unit volume predicted by the initial second prediction model and the sample energy per unit volume; stopping training when the initial second prediction model satisfies a second termination condition in a certain second iteration; wherein the second termination condition includes at least one of the value of the second loss function less than a threshold, performing a certain number of iterations, the second loss function converges, a probability corresponding to the sample energy per unit volume value exceeding a preset probability threshold among predicted values output by the initial second prediction model.

7. The method of claim 1, wherein based on the difference between the first energy per unit volume and the second energy per unit volume, determining whether the first energy per unit volume and the second energy per unit volume are accurate through a deviation determination model comprises:

obtaining an ambient temperature and air oxygen content of the target natural gas when provided for use, and a transmission rate of the target natural gas when provided; and based on the ambient temperature, the air oxygen content, the transmission rate, and the difference between the first energy per unit volume and the second energy per unit volume, determining whether the first energy per unit volume and the second energy per unit volume are accurate by the deviation determination model.

8. The method of claim 1, wherein a deviation coefficient is determined by the deviation determination model based on the difference between the first energy per unit volume and the second energy per unit volume; and the method further comprises:

in response to determining that the first energy per unit volume and the second energy per unit volume are inaccurate, obtaining corrected energy per unit volume by a correction model based on the first energy per unit volume, the second energy per unit volume and the deviation coefficient.

9. The method of claim 8, wherein a training process of the correction model comprises:

obtaining at least one fourth training sample, wherein each of the at least one fourth training sample includes the sample first energy per unit volume of the sample natural gas, the sample second energy per unit volume, the sample deviation coefficient corresponding to the sample natural gas and the sample energy per unit volume of the sample natural gas, wherein the sample energy per unit volume value is determined by the actual combustion of the sample natural gas, wherein the at least one processor specifies an energy per unit volume value of the actual combustion of the sample natural gas as the sample energy per unit volume value; and obtaining the correction model by training an initial correction model based on the at least one fourth training sample, wherein a training of the initial correction model includes one or more fourth iterations, and each fourth iteration includes updating model parameters of the initial correction model based on the fourth training sample such that a value of a fourth loss function is smaller; wherein the fourth loss function is used to characterize a difference between an energy per unit volume predicted by the initial correction model and the sample energy per unit volume; stopping training when the initial correction model satisfies a fourth termination condition in a certain fourth iteration; wherein the fourth termination condition includes at least one of the value of the fourth loss function less than a threshold, performing a certain number of iterations, the fourth loss function converges, a probability corresponding to the sample energy per unit volume value exceeding a preset probability threshold among predicted values output by the initial correction model.

10. The method of claim 1, wherein the determining, based on the carbon content, the first energy per unit volume of the target natural gas comprises:
   obtaining a correspondence between a carbon content and energy per unit volume of natural gas; and
   determining the first energy per unit volume based on the correspondence between the carbon content and the energy per unit volume of the natural gas.

11. The method of claim 1, wherein the determining the second energy per unit volume of the target natural gas based on the combustible component information comprises:
   obtaining a correspondence between the combustible component information and the energy per unit volume of the natural gas; and
   determining the second energy per unit volume energy based on the correspondence between the combustible component information and the energy per unit volume of the natural gas.

12. A system for measuring energy of natural gas based on a reduced data deviation, comprising:
   at least one storage device including a set of instructions;
   at least one processor in communication with the at least one storage device, wherein the at least one processor processes data and/or information obtained from a metering device of natural gas and/or the at least one storage device; wherein the metering device of natural gas is configured to collect data related to natural gas; wherein the metering device of natural gas includes a carbon content detecting device and a volume detecting device; wherein the carbon content detecting device includes a chromatographic detector, and the volume detecting device includes a ultrasonic volume measuring instrument; wherein the carbon content detecting device is configured to obtain a carbon content of natural gas, and the volume detecting device is configured to obtain a volume of natural gas,
   wherein when executing the set of instructions, the at least one processor is configured to cause the system to perform at least one operation, comprising:
   obtaining, by the carbon content detecting device, a carbon content of target natural gas when provided for use, a carbon content of target natural gas when provided for use, and obtaining, by the volume detecting device, a volume of the target natural gas when provided for use;
   determining first energy per unit volume of the target natural gas based on the carbon content, wherein to determine the first energy per unit volume of the target natural gas based on the carbon content, the at least one processor is further configured to cause the system to perform operation including: extracting a carbon element energy release coefficient in a first preset database, and obtaining the first energy per unit volume based on the carbon content and the carbon element energy release coefficient;
   obtaining combustible component information of the target natural gas, and determining second energy per unit volume of the target natural gas based on the combustible component information;
   determining a difference between the first energy per unit volume and the second energy per unit volume;
   based on the difference between the first energy per unit volume and the second energy per unit volume, determining whether the first energy per unit volume and the second energy per unit volume are accurate by a deviation determination model, wherein the deviation determination model is a model for determining whether there is a deviation between different energy per unit volume, and a training process of the deviation determination model comprises:
   obtaining at least one first training sample, wherein each of the at least one first training sample includes a sample combustible component information of sample natural gas, a sample ambient temperature and a sample air oxygen content of the sample natural gas when provided for use, a sample transmission rate of the sample natural gas when provided, and a sample energy per unit volume value of the sample natural gas, wherein the sample energy per unit volume value is determined by an actual combustion of the sample natural gas; determining predictive sample energy per unit volume of the sample natural gas based on the sample first energy per unit volume and the sample second energy per unit volume; determining a difference between the predictive sample energy per unit volume and the sample energy per unit volume; determining a label of the first training sample by comparing the difference between the predictive sample energy per unit volume and the sample energy per unit volume; wherein if the difference between the predictive sample energy per unit volume and the sample energy per unit volume is greater than a preset threshold, the label of the first training sample is that the sample first energy per unit volume and the sample second energy per unit volume are inaccurate; if the difference between the predictive sample energy per unit volume and the sample energy per unit volume is less than or equal to the preset threshold, the label of the first training sample is that the sample first energy per unit volume and the sample second energy per unit volume are accurate; and
   obtaining the deviation determination model by training an initial deviation determination model based on the at least one first training sample, wherein a training of the initial deviation determination model includes one or more third iterations, each of the one or more third iterations includes updating model parameters of the initial deviation determination model based on the at least one first training sample such that a value of a third loss function is smaller; wherein the third loss function is used to characterize a difference between a predicted result of whether the sample first energy per unit volume and the sample second energy per unit volume are accurate, which is output by the initial deviation determination model, and the label of the first training sample; stopping training when the initial deviation determination model satisfies a third termination condition in a certain third iteration; and
   in response to determining that the first energy per unit volume and the second energy per unit volume are accurate, determining energy of the target natural gas based on the first energy per unit volume, the second energy per unit volume, and the volume of the target natural gas.

13. The system of claim 12, wherein the metering device of natural gas further includes a temperature monitoring device, an oxygen concentration monitoring device, a natural gas transmission rate monitoring device, which are arranged on a natural gas pipeline or around the natural gas pipeline, wherein to determine, based on the carbon content, the first energy per unit volume of the target natural gas, the at least one processor is further configured to cause the system to perform at least one operation comprising:

obtaining, by the temperature monitoring device, an ambient temperature of the target natural gas when provided for use, obtaining, by the oxygen concentration monitoring device, an air oxygen content of the target natural gas when provided for use, and obtaining, by the natural gas transmission rate monitor, a transmission rate of the target natural gas when provided; and determining the first energy per unit volume by a first prediction model based on the ambient temperature, the air oxygen content, the transmission rate, and the carbon content.

14. The system of claim 13, wherein a training process of the first prediction model comprises:

obtaining at least one second training sample, wherein each of the at least one second training sample includes a sample carbon content of the sample natural gas, the sample ambient temperature and the sample air oxygen content of the sample natural gas when provided for use, the sample transmission rate of the sample natural gas when provided and the sample energy per unit volume value of the sample natural gas, wherein the sample energy per unit volume value is determined by the actual combustion of the sample natural gas, wherein the at least one processor specifies an energy per unit volume value of the actual combustion of the sample natural gas as the sample energy per unit volume value; and obtaining the first prediction model by training an initial first prediction model based on the at least one second training sample, wherein a training of the first prediction model includes one or more first iterations, and each first iteration includes updating model parameters of the initial first prediction model based on the second training sample such that a value of a first loss function is smaller; wherein the first loss function is used to characterize a difference between the first energy per unit volume predicted by the initial first prediction model and the sample energy per unit volume; stopping training when the initial first prediction model satisfies a first termination condition in a certain first iteration; wherein the first termination condition includes at least one of the value of the first loss function less than a threshold, performing a certain number of iterations, the first loss function converges, a probability corresponding to the sample energy per unit volume value exceeding a preset probability threshold among predicted values output by the initial first prediction model.

15. The system of claim 12, wherein to determine the second energy per unit volume of the target natural gas based on the combustible component information, the at least one processor is configured to cause the system to perform at least one operation comprising:

obtaining an ambient temperature and air oxygen content of the target natural gas when provided for use, and a transmission rate of the target natural gas when provided; and determining the second energy per unit volume by a second prediction model based on the ambient temperature, the air oxygen content, the transmission rate, and the combustible component information.

16. The system of claim 12, wherein based on the difference between the first energy per unit volume and the second energy per unit volume, to determine whether the first energy per unit volume and the second energy per unit volume are accurate through a deviation determination model, the at least one processor is configured to cause the system to perform at least one operation comprising:

obtaining an ambient temperature and air oxygen content of the target natural gas when provided for use, and a transmission rate of the target natural gas when provided; and determining whether the first energy per unit volume and the second energy per unit volume are accurate by the deviation determination model, based on the ambient temperature, the air oxygen content, the transmission rate, and the difference between the first energy per unit volume and the second energy per unit volume.

17. The system of claim 12, wherein a training process of the deviation determination model comprises:

obtaining at least one first training sample, wherein each of the at least one first training sample includes a difference between the sample first energy per unit volume and the sample second energy per unit volume of the sample natural gas, a sample ambient temperature and a sample air oxygen content of the sample natural gas when provided for use, a sample transmission rate of the sample natural gas when provided, and a sample energy per unit volume value of the sample natural gas, wherein the sample energy per unit volume value is determined by an actual combustion of the sample natural gas; and training the deviation determination model based on the at least one first training sample.

18. A non-transitory computer readable medium storing instructions, when executed by at least one processor, causing the at least one processor to implement a method comprising:

obtaining, by a carbon content detecting device, a carbon content of target natural gas when provided for use, a carbon content of target natural gas when provided for use, and obtaining, by a volume detecting device, a volume of the target natural gas when provided for use, wherein the carbon content detecting device is configured to obtain a carbon content of natural gas, and the volume detecting device includes a ultrasonic volume measuring instrument;

determining first energy per unit volume of the target natural gas based on the carbon content, wherein the determining first energy per unit volume of the target natural gas based on the carbon content includes: extracting a carbon element energy release coefficient in a first preset database, and obtaining a first unit volume energy based on the carbon content and the carbon element energy release coefficient of the target natural gas;

obtaining combustible component information of the target natural gas, and determining second energy per unit volume of the target natural gas based on the combustible component information;

determining a difference between the first energy per unit volume and the second energy per unit volume;

based on the difference between the first energy per unit volume and the second energy per unit volume, determining whether the first energy per unit volume and the second energy per unit volume are accurate by a deviation determination model, wherein the deviation determination model is a model for determining whether there is a deviation between different energy per unit volume, and a training process of the deviation determination model comprises:

obtaining at least one first training sample, wherein each of the at least one first training sample includes a difference between the sample first energy per unit volume and the sample second energy per unit volume of the sample natural gas, a sample ambient temperature and a sample air oxygen content of the sample natural gas when provided for use, a sample transmission rate of the sample natural gas when provided, and a sample energy per unit volume value of the sample natural gas, wherein the sample energy per unit volume value is determined by an actual combustion of the sample natural gas; determining predictive sample energy per unit volume of the sample natural gas based on the sample first energy per unit volume and the sample second energy per unit volume; determining a difference between the predictive sample energy per unit volume and the sample energy per unit volume; determining a label of the first training sample by comparing the difference between the predictive sample energy per unit volume and the sample energy per unit volume; wherein if the difference between the predictive sample energy per unit volume and the sample energy per unit volume is greater than a preset threshold, the label of the first training sample is that the sample first energy per unit volume and the sample second energy per unit volume are inaccurate; if the difference between the predictive sample energy per unit volume and the sample energy per unit volume is less than or equal to the preset threshold, the label of the first training sample is that the sample first energy per unit volume and the sample second energy per unit volume are accurate; and obtaining the deviation determination model by training an initial deviation determination model based on the at least one first training sample, wherein a training of the initial deviation determination model includes one or more third iterations, each of the one or more third iterations, includes updating model parameters of the initial deviation determination model based on the at least one first training sample such that a value of a third loss function is smaller; wherein the third loss function is used to characterize a difference between a predicted result of whether the sample first energy per unit volume and the sample second energy per unit volume are accurate, which is output by the initial deviation determination model and a label of the first training sample; stopping training when the initial deviation determination model satisfies a third termination condition in a certain third iteration; and in response to determining that the first energy per unit volume and the second energy per unit volume are accurate, determining energy of the target natural gas based on the first energy per unit volume, the second energy per unit volume, and the volume of the target natural gas.

\* \* \* \* \*